US006841145B2

(12) United States Patent
Horvitz et al.

(10) Patent No.: US 6,841,145 B2
(45) Date of Patent: Jan. 11, 2005

(54) CESERT GENES, PROTEINS, AND MODULATORY COMPOUNDS

(75) Inventors: H. Robert Horvitz, Auburndale, MA (US); Rajesh Ranganathan, Seattle, WA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/843,598

(22) Filed: Apr. 26, 2001

(65) Prior Publication Data

US 2002/0010944 A1 Jan. 24, 2002

Related U.S. Application Data

(60) Provisional application No. 60/200,549, filed on Apr. 26, 2000.

(51) Int. Cl.$^7$ .................. A61K 49/00; A61K 67/00; A01K 67/033

(52) U.S. Cl. .................. 424/9.2; 424/9.1; 800/8

(58) Field of Search .................. 424/9.1, 9.2; 800/8, 800/3, 13

(56) References Cited

U.S. PATENT DOCUMENTS 5,583,008 A    12/1996 Johnson et al.

OTHER PUBLICATIONS

Ali et al., "Ionotropic and Metabotropic Activation of a Neuronal Chloride Channel by Serotonin and Dopamine in the Leech *Hirudo medicinalis*," *Journal of Physiology* 509:211–219 (1998).
De Montigny et al., "Tricyclic Antidepressants: Long–Term Treatment Increases Responsitivity of Rat Forebrain Neurons to Serotonin," *Science* 202:1303–1306 (1978).
Garner et al., "Serotonin Activates Cl⁻Channels in the Apical Membrane of Rat Choroid Plexus Epithelial Cells," *Eur. J. Pharmacol.* 239:31–37 (1993).
Hung et al., "Regulation of Mouse Choroid Plexus Apical Cl⁻ and K⁺Channels by Serotonin," *Brain Res.* 617:285–295 (1993).
Koumenis et al., "Identification of Three Proteins in the Eye of *Aplysia*, Whose Synthesis Is Altered by Serotonin (5–HT)," *Journal of Biological Chemistry* 270:14619–14627 (1995).
Lessmann et al., "Development of Serotonin–Induced Ion Currents in Identified Embryonic Retzius Cells From the Medicinal Leech (*Hirudo medicinalis*)," *J. Neurosci.* 11:800–809 (1991).
Lessmann et al., "Two Kinetically Distinct 5–Hydroxytryptamine–Activated Cl⁻Conductances at Retzius P–Cell Synapses of the Medicinal Leech," *J. Neurosci.* 15:1496–1505 (1995).

Liu et al., "High–Throughput Isolation of *Caenorhabditis elegans* Deletion Mutants," *Genome Research* 9:859–867 (1999).
Madison et al., "Phorbol Esters Block a Voltage–Sensitive Chloride Current in Hippocampal Pyramidal Cells," *Nature* 321:695–697 (1986).
Munsch and Schlue, "Intracellular Chloride Activity and the Effect of 5–Hydroxytryptamine on the Chloride Conductance of Leech Retzius Neurons," *Eur. J. Neurosci.* 5:1551–1557 (1993).
Parra et al., "How Many Subtypes of Inhibitory Cells in the Hippocampus?," *Neuron* 20:983–993 (1998).
Scrogin et al., "Multiple Receptor Subtypes Mediate the Effects of Serotonin on Rat Subfornical Organ Neurons," *Am. J. Physiol.* R2035–R2042 (1998).
Hamdan et al., "Characterization of a Novel Serotonin Receptor from *Caenorhabditis elegans*: Cloning and Expression of Two Splice Variants," *Journal of Neurochemistry*, 72:1372–1383, (1999).
Huang et al., "Alternative–Splicing of Serotonin Receptor Isoforms in the Pharynx and Muscle of the Parasitic Nematode, *Ascaris suum*, " *Molecular and Biochemical Parasitology*, 101:95–106, (1999).
Olde and McCombie, "Molecular Cloning and Functional Expression of a Serotonin Receptor from *Caenorhabditis elegans*," *Journal of Molecular Neuroscience*, 7:53–62, (1997).
Sze et al., "Food and Metabolic Signalling Defects in a *Caenorhabditis elegans* Serotonin–Synthesis Mutant," *Nature*, 403: 560–564, (2000).
Trim et al., "Characterization of 5–HT Receptors in the Parasitic Nematode, *Ascaris suum*," *Parasitology*, 122:207–217, (2001).
Williams et al., "Identification of a Novel 5–HT$_N$(Nematoda) Receptor from *Ascaris suum* Muscle," *Comp. Biochem. Physiol.* 101C:469–474, (1992).
Blakely et al., "Cloning and Expression of a Functional Serotonin Transporter from Rat Brain," *Nature* 354:66–70 (1991).
Choy and Thomas, "Fluoxetine–Resistant Mutants in *C. elegans* Define a Novel Family of Transmembrane Proteins," *Mol. Cell* 4:143–152 (1999).
Corey et al., "A Cocaine–Sensitive *Drosophila* Serotonin Transporter: Cloning, Expression, and Electrophysiological Characterization," *Proc. Natl. Acad. Sci. USA* 91:1188–1192 (1994).

(List continued on next page.)

*Primary Examiner*—Scott D. Priebe
(74) *Attorney, Agent, or Firm*—Clark & Elbing, LLP; Kristina Bieker-Brady, P.C.

(57) ABSTRACT

The invention features substantially pure nucleic acid sequences encoding wild-type or mutant serotonin retake transporter (SERT) polypeptides, as well as the polypeptides themselves. The invention also features methods for identifying modulators of the biological activity of a SERT and for identifying if such a modulator has a secondary target. In addition, the invention features methods for treating a condition in a subject.

10 Claims, 13 Drawing Sheets-

OTHER PUBLICATIONS

Demchyshyn et al., "Cloning, Expression, and Localization of a Chloride–Facilitated, Cocaine–Sensitive Serotonin Transporter from *Drosophila melanogaster*," *Proc. Natl. Acad. Sci. USA* 91:5158–5162 (1994).

Desai et al., "A Genetic Pathway for the Development of the *Caenorhabditis elegans* HSN Motor Neurons," *Nature* 336:638–646 (1988).

Horvitz et al., "Serotonin and Octopamine in the Nematode *Caenorhabditis elegans*," *Science* 216:1012–1014, (1982).

Mendel et al., "Participation of the Protein $G_o$ in Multiple Aspects of Behavior in *C. elegans*," *Science* 267:1652–1655 (1995).

Ramamoorthy et al., "Antidepressant– and Cocaine–Sensitive Human Serotonin Transporter: Molecular Cloning, Expression, and Chromosomal Localization," *Proc. Natl. Acad. Sci. USA* 90:2542–2546 (1993).

Ranganathan and Horvitz, "*mod–1* and *mod–5*, Two Genes Involved in the Serotonin–Mediated Experience–Dependent Modulation of Locomotion," (Abstract) East Coast *C. elegans* Meeting, Boston, MA, Jun. 6–8, 1998.

Ranganathan et al., "An Ionotropic Serotonin Receptor and a Serotonin Reuptake Transporter Are Involved in Experience–Dependent Modulation of Behavior," (Abstract) Twelfth International *C. elegans* Meeting, Madison, WI, Jun. 2–6, 1999.

Ranganathan et al., "MOD–1 is a Serotonin–Gated Chloride Channel that Modulates Locomotory Behaviour in *C. elegans*," *Nature* 408:470–475 (2000).

Sawin, "Genetic and Cellular Analysis of Modulated Behaviors in *Caenorhabditis elegans*," Massachusetts Institute of Technology, (Ph.D. Thesis) (1996).

Sawin et al., "*C. elegans* Locomotory Rate Is Modulated by the Environment through a Dopaminergic Pathway and by Experience through a Serotonergic Pathway," *Neuron* 26:619–631, (2000).

Ségalat et al., "Modulation of Serotonin–Controlled Behaviors by $G_o$ in *Caenorhabditis elegans*," *Science* 267:1648–1651 (1995).

Weinshenker et al., "Genetic and Pharmacological Analysis of Neurotransmitters Controlling Egg Laying in *C. elegans*," *J. Neurosci.* 15:6975–6985 (1995).

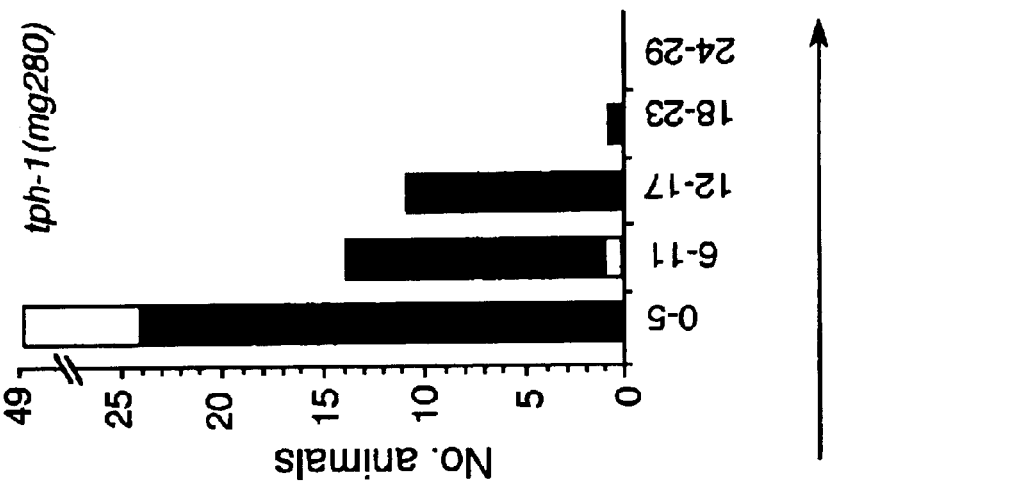
FIG. 6C tph-1(mg280)
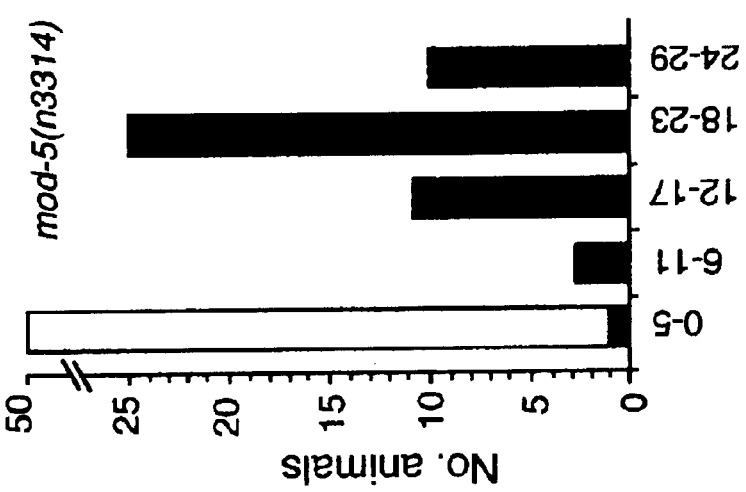
FIG. 6B mod-5(n3314)
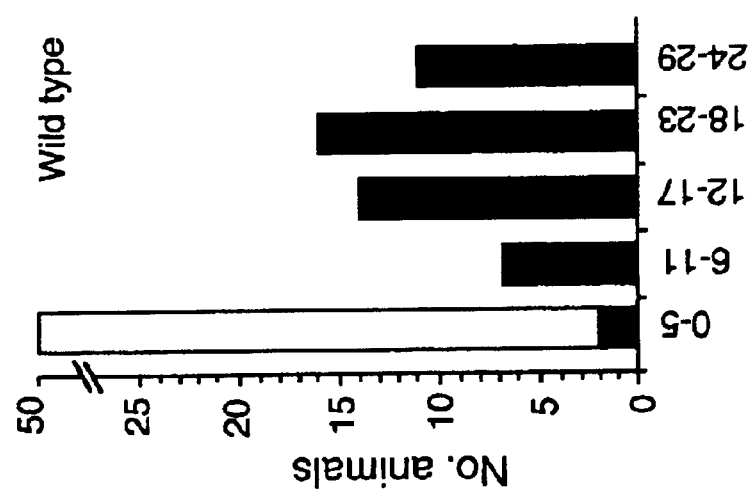
FIG. 6A Wild type

CESERT GENES, PROTEINS, AND MODULATORY COMPOUNDS

CROSS REFERENCE TO RELATED APPLICATIONS

This application claims priority from U.S. provisional patent application Ser. No. 60/200,549, filed on Apr. 26, 2000, the disclosure of which is hereby incorporated by reference.

STATEMENT AS TO FEDERALLY SPONSORED RESEARCH

This research was funded, in part, by NIH Grant R37GM24663. The U.S. government has certain rights to the invention.

FIELD OF THE INVENTION

The field of this invention is the identification and analysis of compounds that modulate biological activity.

BACKGROUND OF THE INVENTION

The functions of serotonin in mammals are numerous and include control of appetite, sleep, memory and learning, temperature regulation, mood (e.g., depression), behavior (including sexual and hallucinogenic behavior), cardiovascular function, muscle contraction, and endocrine regulation. Small molecules that manipulate serotonin neurotransmission include drugs of major importance and provide a sizable percentage of the revenue of the pharmaceutical industry. These drugs include the first generation tricyclic antidepressants, such as amytryptyline, imipramine, and chlomipramine; serotonin selective reuptake inhibitors (SSRIs), such as fluoxetine, sertraline, and paroxetine; monoamine oxidase inhibitors; other antidepressants, such as citalopram; migraine medications, such as sumatriptan and rizatriptan; and anti-emetics, such as granisetron and ondansetron. The site of action of the reuptake inhibitors and many of the other drugs listed above is purported to be the serotonin reuptake transporter (SERT). SERTs have been cloned from numerous species, including *Drosophila melanogaster*, mice, and humans. The cloning of SERTs from numerous species has facilitated extensive structure-function and pharmacological studies, where the conservation of amino acid residues during evolution has provided key insights into the regions of the transporter that are relevant for serotonin binding and transport, as well as for the binding of the various drugs that affect the function of the transporter.

Drugs acting at SERTs, however, have many side effects, and very little is known about the mechanism(s) causing these side effects. Drug side effects are detrimental in several ways. They prevent drugs from being used at doses that might be more effective at treating the primary indication, and sometimes the side effects may be so prohibitively noxious that a particular compound never reaches the market, or can only be used with a subset of the patient population for which it might otherwise be effective. An understanding of the causes of these side effects and determination of the genes and pathways that are affected would allow the use of rational drug design and/or combination drug therapy, leading to more efficient, safe, and better tolerated drugs.

SUMMARY OF THE INVENTION

The invention features methods for testing whether a compound that modulates CeSERT activity has a secondary target. These methods are useful in determining if a compound has any side effects, as a consequence of interacting with a secondary target, and will therefore aid in the identification of therapeutic compounds that provide optimal serotonergic biological function with minimal side effects. In addition, the present invention encompasses *C. elegans* SERT (CeSERT) genes and polypeptides, as well as methods for identifying compounds that modulate CeSERT biological activity. These compounds may be used as therapeutic agents in the treatment of serotonin-mediated conditions.

Accordingly, the first aspect of the invention features a method for determining the activity range of a test compound, which modulates the uptake of serotonin by a serotonin reuptake transporter, against a secondary target. This method includes the steps of: (a) contacting a first nematode expressing a mutated CeSERT polypeptide, where the mutated CeSERT polypeptide has a reduced capacity to take up serotonin relative to wild-type, with the compound; (b) assaying a defined behavior of the first nematode; (c) assaying the defined behavior of a second nematode not contacted with the compound; and (d) comparing the defined behavior of the first nematode to that of the second nematode, where a difference in the defined behavior between the first and second nematode indicates that the compound has a secondary target.

In a preferred embodiment of this aspect of the invention, steps (a) to (d) are repeated using first and second nematodes selected from a panel of nematodes expressing mutant CeSERT polypetides, wherein the mutant CeSERT polypeptides differ from the mutated CeSERT polypeptide of step (a). For example, a mutated CeSERT polypeptide may be a complete loss-of-function. In addition, the mutated CeSERT polypeptide may be a CeSERT(n822) polypeptide, a CeSERT(n823) polypeptide, or a CeSERT(n3314) polypeptide.

In another embodiment, the method of this aspect may include a liquid locomotion assay. Furthermore, the defined behavior may be movement, pharyngeal pumping, egg-laying, nose contraction, or defecation.

In an additional embodiment, the compound is from a class of compounds selected from a group including antidepressants, migraine medications, and anti-emetics. For example, an antidepressant may be a selective serotonin reuptake inhibitor, a tricyclic antidepressant, or a monoamine oxidase inhibitor. In another embodiment of this aspect, the test compound may administered at more than one concentration.

In a further aspect, the invention features a method, e.g., a liquid locomotion assay, for identifying a compound that modulates the biological activity of a serotonin reuptake transporter. This method includes the steps of: (a) exposing at least one first nematode to a test compound; (b) quantifying the number of these first nematodes exhibiting a defined behavior after exposure to the test compound; (c) quantifying the number of second nematodes exhibiting the defined behavior, wherein the second, control nematodes are not exposed to the test compound; and (d) comparing the number of the first or second nematodes exhibiting the defined behavior to the total number of first or second nematodes to obtain the relative number of first or second nematodes exhibiting the defined behavior, where a difference in the relative number of first and second nematodes exhibiting the defined behavior indicates that a compound modulates the biological activity of a serotonin reuptake transporter. However, the number of the first and second nematodes not exhibiting the defined behavior may also be quantified.

In a preferred embodiment of this aspect of the invention, the defined behavior may be movement (e.g., swimming).

In addition, the first and second nematodes of this aspect of the invention may express a wild-type or a mutated CeSERT gene. For example, the mutated CeSERT gene may express a truncated CeSERT polypeptide, which in turn may function as a wild-type CeSERT polypeptide. However, the mutated CeSERT gene may also be a CeSERT(n822), CeSERT(n823), or CeSERT(n3314) gene. In a further embodiment, the first and second nematode may express a mammalian SERT gene such as a human hSERT gene.

In another preferred embodiment of this aspect of the invention, the test compound is applied at more than one concentration. In addition, the second nematode may be, for example, receiving serotonin or a placebo. Furthermore, a compound affecting the serotonergic pathway may be administered in addition to the test compound.

In a further preferred embodiment, the first and second nematode has been bacterial-lawn deprived prior to beginning the assay and the test compound may be administered in the presence or absence of serotonin.

In additional preferred embodiments, the modulation is agonistic, resulting in increased serotonin reuptake transporter biological activity relative to a control, or antagonistic, resulting in decreased serotonin reuptake transporter biological activity relative to a control.

In another embodiment, a condition in a subject is treated by administering, to a subject, a compound that was identified according to the method of this aspect of the invention. Examples of conditions that may be treated according to the method of this aspect of the invention include loss of appetite, gain of appetite, insomnia, an inability to wake up, memory loss, loss of the ability to learn, decreased ability to regulate body temperature, abnormal mood, abnormal behavior, abnormal cardiovascular function, abnormal muscle contraction, abnormal endocrine regulation, nausea, vomiting, gastrointestinal cramps, a migraine, a panic disorder, and an obsessive compulsive disorder. An abnormal mood may be, for example, increased depression or mania, whereas abnormal behavior may be, for example, sexual or hallucinogenic. Furthermore, the compound may be an agonist, resulting in increased serotonin reuptake transporter biological activity relative to a control, or an antagonist, resulting in decreased serotonin reuptake transporter biological activity relative to a control.

In an additional aspect, the invention features a substantially pure nucleic acid encoding a CeSERT polypeptide that is at least 45% identical to SEQ ID NO:5, where the CeSERT polypeptide modulates the uptake of serotonin by a synaptic neuron.

A further aspect of the invention features a substantially pure nucleic acid encoding a CeSERT polypeptide that is at least 45% identical to SEQ ID NOS:6, 7 or 8, where the CeSERT polypeptide has a reduced capacity to modulate the uptake of serotonin by a synaptic neuron, relative to wild-type. For example, the substantially pure nucleic acid may encode a polypeptide containing a stop codon at a position equivalent to position 225 of SEQ ID NO:6, or a polypeptide containing a serine at a position equivalent to position 569 of SEQ ID NO:7. In a preferred embodiment of this aspect of the invention, the substantially pure nucleic acid encodes a polypeptide including SEQ ID NO:8.

In another aspect, the invention features a *Caenorhabditis elegans* strain including a CeSERT nucleic acid, where this CeSERT nucleic acid encodes a polypeptide that is at least 45% identical to a polypeptide of SEQ ID NOS:6, 7, or 8. The CeSERT(n822) and CeSERT(n823) polypeptides are specifically excluded from this aspect of the invention. In a preferred embodiment of this aspect, the *Caenorhabditis elegans* encodes a CeSERT(n3314) polypeptide.

Another aspect of the invention features a substantially pure CeSERT polypeptide that is at least 45% identical to SEQ ID NO:5, where the CeSERT polypeptide modulates the uptake of serotonin by a synaptic neuron.

In a further aspect, the invention features a substantially pure CeSERT polypeptide that is at least 45% identical to SEQ ID NOS:6, 7 or 8, where this CeSERT polypeptide has a reduced capacity to modulate the uptake of serotonin by a synaptic neuron. In a preferred embodiments of this aspect of the invention, the substantially pure CeSERT polypeptide contains a stop codon at a position equivalent to position 225 of SEQ ID NO:6 or contains a serine at a position equivalent to position 569 of SEQ ID NO:7. In addition the substantially pure CeSERT polypeptide may include SEQ ID NO:8.

The final aspect, the invention features a transgenic animal including a CeSERT nucleic acid of SEQ ID NOS:1, 2, 3, or 4. This transgenic animal may be, for example, a nematode or a mammal, such as a mouse. In other preferred embodiments, the transgenic animal over-expresses the CeSERT nucleic acid, or expresses a dominant-negative CeSERT polypeptide.

Definitions

By a "substantially pure nucleic acid" or "substantially pure DNA" is meant a nucleic acid that is free of the genes that, in the naturally-occurring genome of the organism from which the nucleic acid of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (e.g., a cDNA or a genomic or cDNA fragment produced by PCR or restriction endonuclease digestion) independent of other sequences. It also includes recombinant DNA that is part of a hybrid gene encoding additional polypeptide sequence.

By a "SERT gene" or "mod-5 gene" is meant a nucleic acid sequence encoding a polypeptide that is a serotonin reuptake transporter. In one embodiment, the SERT gene is a *C. elegans* gene and is known as a "CeSERT gene." In another embodiment the SERT gene is a human gene and is known as an "hSERT gene."

By a "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably the polypeptide is a serotonin reuptake transporter polypeptide that is at least 75%, more preferably at least 90%, and most preferably at least 99%, by weight, pure. A substantially pure serotonin reuptake transporter polypeptide may be obtained, for example, by extraction from a natural source (e.g., a neuron or smooth muscle cell) by expression of a recombinant nucleic acid encoding a serotonin reuptake transporter polypeptide, or by chemically synthesizing the protein. Purity can be assayed by any appropriate method (e.g., by column chromatography, polyacrylamide gel electrophoresis, agarose gel electrophoresis, optical density, or HPLC analysis).

A protein is substantially free of naturally associated components when it is separated from those contaminants that accompany it in its natural state. Thus, a protein that is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

By a "SERT protein," "SERT polypeptide," "MOD-5 protein," or "MOD-5 polypeptide" is meant a polypeptide or fragment thereof, encoded by a SERT gene. In one embodiment, the SERT protein or polypeptide is from C. elegans, and such a protein or polypeptide is known as "CeSERT." In another embodiment, the SERT protein is human, and is also referred to as "hSERT."

By a "CeSERT(n822) gene" or "mod-5(n822) gene" is meant a CeSERT gene having the sequence of SEQ ID NO:2.

By a "CeSERT(n822) polypeptide" or "MOD-5(n822) polypeptide" is meant a CeSERT polypeptide having the sequence of SEQ ID NO:6.

By a "CeSERT(n823) gene" or "mod-5(n823) gene" is meant a CeSERT gene having the sequence of SEQ ID NO:3.

By a "CeSERT(n823) polypeptide" or "MOD-5(n823) polypeptide" is meant a CeSERT polypeptide having the sequence of SEQ ID NO:7.

By a "CeSERT(n3314) gene" or "mod-5(n3314) gene" is meant a CeSERT gene having the sequence of SEQ ID NO:4.

By a "CeSERT(n3314) polypeptide" or "MOD-5(n3314) polypeptide" is meant a CeSERT polypeptide having the sequence of SEQ ID NO:8.

By "substantially identical" is meant a polypeptide or nucleic acid exhibiting at least 45%, more preferably 55%, 60%, 70%, 80%, 90%, and most preferably 95% identity to a reference amino acid sequence (for example, an amino acid sequence described herein) or nucleic acid sequence (for example, a nucleic acid sequence described herein). For polypeptides, the length of comparison sequences will generally be at least 15 amino acids, preferably at least 20 amino acids, more preferably at least 35 amino acids, and most preferably over the full length of the polypeptide. For nucleic acids, the length of comparison sequences will generally be at least 60 nucleotides, preferably at least 75 nucleotides, more preferably 110 nucleotides, and most preferably over the full length of the nucleic acid sequence. As used herein a nucleic acid or polypeptide sequence may be substantially identical to a wild-type or mutated CeSERT nucleic acid or polypeptide.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). These software programs match identical or similar sequences by assigning degrees of identity to various substitutions, deletions, and/or other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "polypeptide analogs," as referred to herein, is meant a polypeptide that generally exhibits at least 85%, more preferably 90%, and most preferably 95% or even 99% identity with all or part of a naturally-occurring amino acid sequence, for example the amino acid sequence of SEQ ID NOS:5, 6, 7, and 8. The length of sequence comparison is at least 15 amino acid residues, preferably at least 25 amino acid residues, and more preferably more than 35 amino acid residues.

As used herein, the term "polypeptide fragment" means at least 20 contiguous amino acids, preferably at least 30 contiguous amino acids, more preferably at least 50 contiguous amino acids, and most preferably at least 60 to 80 or more contiguous amino acids.

By "degenerate variants" is meant nucleic acid sequences that encode the same polypeptide as a result of the redundancy of the genetic code. For example, the codon for leucine can be any one of six different codons, and the nucleotides comprising these six codons are degenerate variants.

By "high stringency conditions" is meant conditions that are commonly understood in the art as stringent. An exemplary set of high stringency conditions include a temperature of 60–70° C. (preferably about 65° C.) and a salt concentration of 0.70 M to 0.80 M (preferably about 0.75 M). Further exemplary conditions include hybridization conditions that (1) employ low ionic strength and high temperature for washing, for example, 0.015 M NaCl/0.0015 M sodium citrate/0.1% SDS at 50° C.; (2) employ during hybridization a denaturing agent, such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 5× Denhardt's solution, sonicated salmon sperm DNA (50 g/ml), 0.1% SDS, and 10% dextran sulfate at 42° C., with washes at 42° C. in 0.2×SSC and 0.1% SDS. Further examples of stringent conditions can be found in Sambrook, Fritsch and Maniatis, *Molecular Cloning: A Laboratory Manual* (2d ed.), Cold Spring Harbor Press, 1989, or Ausubel et al., *Current Protocols in Molecular Biology*, John Wiley & Sons, New York, N.Y., 1994.

By "treatment" is meant the submission or subjection of an animal, cell, lysate or extract derived from a cell, or molecule derived from a cell to a test compound or stimulus to a serotonin-mediated response.

By a "test compound" is meant a chemical, be it naturally-occurring or artificially-derived, that is surveyed for its ability to modulate serotonin-mediated cellular responses, by employing one of the assay methods described herein. Test compounds may include, for example, peptides, polypeptides, synthetic organic molecules, naturally-occurring organic molecules, nucleic acid molecules, and components thereof.

By a "control compound" is meant a chemical, be it naturally-occurring or artificially derived, that has a known effect, or no effect, on an organism. For example, a control compound may be a placebo.

By "treat" is meant to submit or subject an animal, cell, lysate or extract derived from a cell, or molecule derived from a cell to a test compound or stimulus to a serotonin-mediated response.

"Mutated" or "mutant," as used herein, refers to different from what normally appears, occurs, or functions. As used herein, the term refers to a nucleic acid or polypeptide containing a sequence that is different from the wild-type sequence. Such a difference in sequence may be, for example, a single nucleic or amino acid change, but it may also include deletions or insertions of multiple nucleic or amino acids. The term mutant also means an organism that carries a mutant nucleic acid or polypeptide sequence. As used herein, the mutant nucleic acid or polypeptide sequence is, for example, CeSERT or hSERT.

By "biological activity" is meant a functional event mediated by a protein. In one embodiment, this includes the level of sensitivity to serotonin (exogenous or endogenous). It also includes interactions of a polypeptide with another polypeptide, as well as events that modify behavior or behavioral states. Such behavior includes, but is not limited to, movement, sexual behavior, mood, or hallucinogenic behavior. Behavioral states include, but are not limited to, loss of appetite, gain of appetite, insomnia, inability to wake up, memory loss, nausea, vomiting, gastrointestinal cramps, ability or inability to learn, body temperature deregulation, migraines, moods, such as depression or mania, panic disorders, obsessive compulsive disorder, abnormal cardiovascular function, abnormal muscle contraction, and abnormal endocrine regulation.

In *C. elegans*, biological activity includes, but is not limited to, locomotion, egg-laying, pharyngeal pumping, nose contraction, and defecation.

By "defined behavior," as used herein, is meant, for example, movement, sexual behavior, mood, or hallucinogenic behavior. In *C. elegans*, "defined behavior" includes, but is not limited to, movement, nose contraction, egg-laying, pharyngeal pumping, and defecation. An example of movement is swimming behavior. In addition, a "defined behavior" may refer to the rate at which a behavior is carried out, for example, the rate of movement or of egg-laying.

As used herein, by "modulates" is meant increasing or decreasing the biological activity. Preferably the biological activity is increased or decreased 10% relative to a control. More preferably the biological activity is increased or decreased 50% relative to a control. Most preferably the biological activity is increased or decreased 90% relative to a control.

By "reduced capacity to take up serotonin," as used herein, is meant a reduction of least 10% in the ability of a cell, for example a synaptic neuron, to take up serotonin, relative to wild-type. More preferably, the reduction is at least 25%, 50%, or 75%. Most preferably, the reduction is at least 85%. However, a "reduced capacity to take up serotonin" may also include a complete inability to take up serotonin.

By "relative number," as used herein, is meant a number that can be used for direct comparisons, for example, a percentage.

By "assaying" is meant analyzing the effect of a treatment or exposure, be it chemical or physical, administered to whole animals or cells derived from such an animal. The material being analyzed may be an animal, a cell, a lysate or extract derived from a cell, or a molecule derived from a cell. The analysis may be, for example, for the purpose of detecting the level of sensitivity of a cell or animal to serotonin, alterations in locomotion, egg-laying, pharyngeal pumping or defecation behaviors of an animal, altered gene expression, altered nucleic acid stability (e.g., mRNA stability), altered protein stability, altered protein levels, altered protein biological activity, or a side effect caused by a compound. The means for analyzing may include, for example, counting movements of an animal under a microscope, observing the behavior of a nematode in the presence of a compound, nucleic acid amplification techniques, utilizing gene chip or DNA array technologies, reporter gene assays, antibody labeling, immunoprecipitation, and phosphorylation assays and other techniques known in the art for conducting the analysis of the invention.

"Liquid locomotion," as used herein, refers to nematodes exhibiting movement, such as swimming behavior, when placed into a liquid.

By a "neuron" is meant a cell of ectodermal embryonic origin derived from any part of the nervous system of an animal. Neurons express well-characterized neuron-specific markers that include neurofilament proteins, MAP2, and class III-tubulin. Included as neurons are, for example, hippocampal, cortical, motor, sensory, sympathetic, septal cholinergic, and cerebellar neurons.

By a "condition" is meant a state of being or feeling. Conditions include, but are not limited to, loss of appetite, gain of appetite, insomnia, inability to wake up, memory loss, nausea, vomiting, gastrointestinal cramps, ability or inability to learn, body temperature deregulation, moods, such as depression or mania, panic disorders, obsessive compulsive disorder, migraine, abnormal sexual or hallucinogenic behavior, abnormal cardiovascular function, abnormal muscle contraction, and abnormal endocrine regulation.

By a "secondary target" is meant any additional site of biological activity acted upon by a compound that is different than the site of biological activity for which the compound is administered. As used herein, a compound that acts upon a secondary target may result in the compound having non-therapeutic side effects. For example, a drug administered as a serotonin reuptake inhibitor, such as fluoxetine, may affect serotonin reuptake transporter-dependent and serotonin reuptake transporter-independent pathways. In this example, the affected serotonin reuptake transporter-independent pathways are "secondary targets."

By "transgenic" is meant any cell or organism that includes a DNA sequence that is inserted by artifice into a cell and becomes part of the genome of the organism that develops from that cell. As used herein, the transgenic organism is generally a transgenic non-human mammal (e.g., a rodent, such a rat or mouse) or invertebrate (e.g., *Caenorhabditis elegans*), and the DNA (transgene) is inserted by artifice into the genome.

By "expose" is meant to allow contact between an animal, cell, lysate or extract derived from a cell, or molecule derived from a cell, and a test compound or activator of a serotonergic response.

By a "post-translational modification" is meant any change to a polypeptide during or after synthesis. Such modifications may include phosphorylation and glycosylation. Post-translational modifications may be naturally occurring (such as during synthesis within a cell), or artificially generated (such as by recombinant or chemical means).

DETAILED DESCRIPTION OF THE INVENTION

Described herein are substantially purified nucleic acid sequences encoding a CeSERT polypeptide or a mutant CeSERT polypeptide, as well as the polypeptides themselves. In addition, methods for identifying modulators of the biological activity of a serotonin reuptake transporter, and identifying if such a modulator has a secondary target are also described below, as are methods for treating a condition in a subject.

The cloning of the CeSERT gene is an important advancement. Since serotonergic neurotransmission is likely to be conserved in *C. elegans* relative to other animals, including *Drosophila melanogaster* and mammals, understanding the function of CeSERT, in the context of the various *C. elegans* behaviors that are modulated by serotonin, allows a molecular/genetic pathway for serotonergic neurotransmission to be defined. In addition, the cloning of the CeSERT gene, and mutations thereof, described herein is useful in identifying residues and regions of importance for both SERT function and for the response of a SERT to a specific drug.

Furthermore, the *C. elegans* strains with mutant CeSERT genes of the present invention can be used as tools for fast and easy, high-throughput screening of compounds that modulate SERTs, and secondary targets or side effects of compounds that modulate SERTs, including currently available drugs, as is described below.

Isolation of Mutants Defective in Serotonin Uptake

Formaldehyde-induced fluorescence (FIF) histochemistry indicates that the *C. elegans* neurosecretory motor neurons (NSMs), located in the pharynx, contain serotonin in their cell bodies and axonal processes (Horvitz et al., *Science* 216:1012–1014, 1982). FIF in the NSMs was more readily observed when animals were preincubated with exogenous serotonin prior to the staining protocol (Horvitz et al.,

*Science* 216:1012–1014, 1982). This observation suggested that the NSMs possess an active uptake system that can concentrate serotonin from the extracellular environment.

Figure 1A:
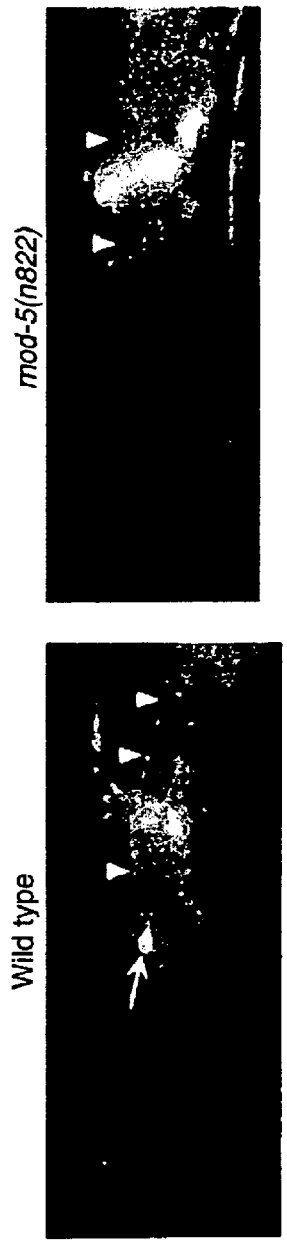
FIG. 1 shows that the NSMs of mod-5 mutants are defective in serotonin uptake. Panel A shows wild-type and mod-5(n822) animals preincubated with exogenous serotonin stained using FIF to visualize serotonin (Sulston et al., *J Comp Neurol* 163:215–226, 1975). The arrow points to a NSM processes. No NSM cell bodies were FIF-positive in mod-5(n822) mutants. Panel B shows NSMs in mod-5(n822) and mod-5(n823) mutants with reduced uptake of exogenous serotonin. At least 100 animals were tested for each genotype in each condition. Error bars indicate the standard error of the sample mean (SEM).

We performed a genetic screen for mutants lacking FIF in the NSMs following preincubation with exogenous serotonin. Two mutations that failed to complement each other, n822 and n823, were isolated. n822 and n823 mutants lacked FIF in the NSM cell bodies after serotonin preincubation but retained FIF in the NSM axonal processes (FIG. 1A). Nomarski optics (Ellis and Horvitz, *Cell* 44:817–829, 1986) revealed that these mutants had NSM cell bodies in their usual positions.

Serotonin can also be detected in *C. elegans* using anti-serotonin antisera, which have proven to be more sensitive than FIF and have allowed the reliable detection of endogenous serotonin in the NSMs and other neurons without requiring preincubation with exogenous serotonin (Desai et al., *Nature* 336:638–646,1988; Loer and Kenyon,*J Neurosci* 13:5407–5417, 1993; Sawin et al., *Neuron* 26:619–623, 2000). We used anti-serotonin antisera to evaluate serotonin reuptake in n822 and n823 mutants. Since endogenous serotonin masks serotonin reuptake in NSMs visualized using anti-serotonin antisera, we used a cat-4(e1141) (catecholamine defective) genetic background to reduce endogenous serotonin levels (Desai et al., *Nature* 336:638–646, 1988; Weinshenker et al., *Neurosci* 15:6975–6985, 1995). cat-4 encodes GTP cyclohydrolase I, which is required for the synthesis of a biopterin co-factor needed for dopamine and serotonin biosynthesis (Kapatos et al., *J Neurochem* 72:669–675, 1999).

Figure 1B:
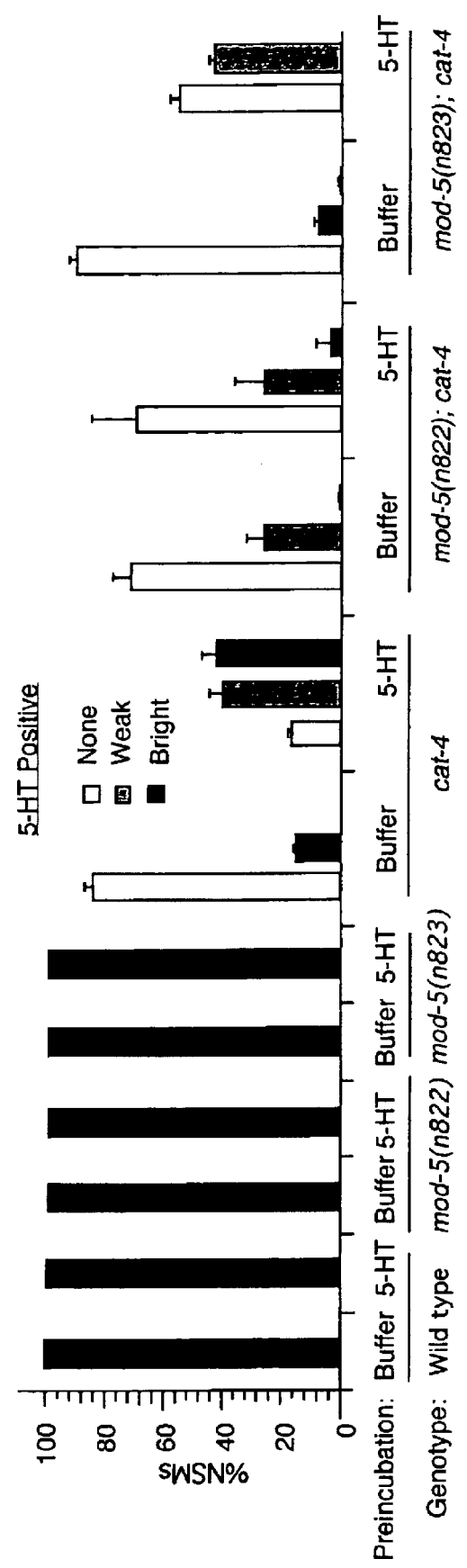

We counted the number of immunoreactive NSMs in cat-4 single and n822; cat-4 and n823; cat-4 double mutants with or without exogenous serotonin preincubation. While NSMs in the cat-4 mutants were capable of serotonin uptake, the NSMs in n822; cat-4 and n823; cat-4 double mutants were partially defective in serotonin uptake (FIG. 1B), confirming our FIF observations. For example, we observed no brightly-fluorescing NSMs in n823; cat-4 mutants pre-incubated with serotonin, while 43% of the NSMs in cat-4 mutants had bright immunofluorescence (FIG. 1B, black bars). That a slight increase in NSM immunoreactivity was observed in n822; cat-4 and n823; cat-4 mutants upon serotonin preincubation indicates that the n822 and n823 mutations do not lead to a complete loss of serotonin uptake. While previous studies did not detect anti-serotonin immunoreactivity in cat-4 mutants (Desai et al., *Nature* 336:638–646, 1988; Loer and Kenyon, *J Neurosci* 13:5407–5417, 1993; Weinshenker et al., *J Neurosci* 15:6975–6985, 1995), we observed, using the same staining protocol as in the previous studies, a small percentage of weakly anti-serotonin-immunoreactive NSMs in cat-4 mutants in the absence of serotonin preincubation (FIG. 1B). This staining is serotonin, since this antibody did not result in any immunoreactivity in tph-1 mutants (see below), which lack the serotonin biosynthetic enzyme tryptophan hydroxylase and are specifically deficient in serotonin (Sze et al., *Nature* 403:561–564, 2000). Our data show that the cat-4 mutation does not lead to a complete loss of serotonin, consistent with the conclusions of Desai et al. (*Nature* 336:638–646, 1988) and Avery and Horvitz (*J Exp. Zool* 253:263–270, 1990).

MOD-5 is Similar to SERTs

The *C. elegans* CeSERT(n823) mutation had previously been mapped to the interval between lin-17 and unc-74 on chromosome I (Sawin, Ph.D. Thesis, Massachusetts Institute of Technology, 1996). mod-5 was mapped further to the genetic interval between lin-17 and unc-11. Transformed rescue of mod-5(n823) was achieved by injecting fragments of genomic DNA, generated by long-PCR, that contained the CeSERT predicted open reading frame. This open reading frame was then sequenced in the mod-5(n822) and mod-5(n823) animals and found to contain point mutations. Subsequently, animals containing the n3314 deletion were isolated and the n3314 allele was shown not to complement the n822 and n823 alleles, thus confirming the cloning of the mod-5 gene.

We used the serotonin hypersensitivity of mod-5 mutants in the liquid swimming assay to map and clone the gene. We mapped mod-5 to an approximately 2.0 map unit interval on chromosome I, between fog-1 and unc-11 (FIG. 3A) (see Example 6). An open reading frame, Y54E10A__154.A, in this region was predicted to encode a protein with similarity to serotonin reuptake transporters (SERTs).

Figures 3A, 3B:
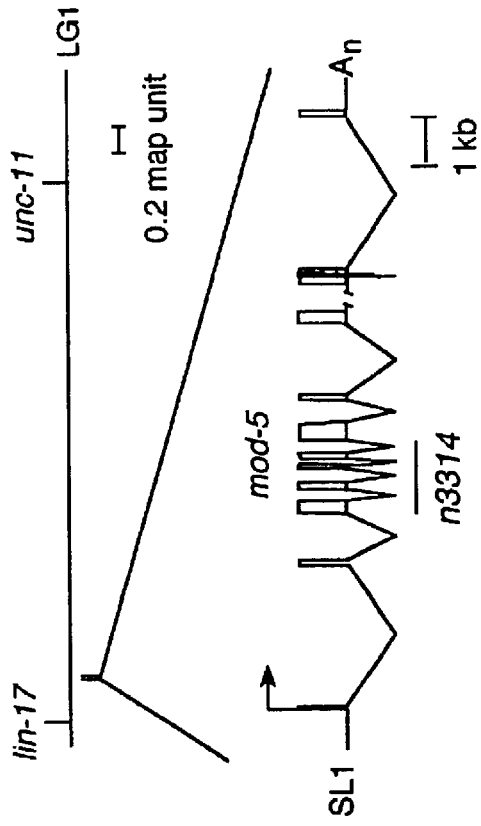
FIG. 3 shows that mod-5 encodes a protein similar to the human and *Drosophila melanogaster* serotonin reuptake transporters. The top of panel A is a genetic map of the mod-5 region of linkage group I (LG I) and the bottom of panel A shows the intron-exon structure of mod-5 (Y54E10A_154.A), inferred from cDNA sequences. The open boxes indicate coding regions, the lines indicate untranslated regions, the arrow shows the direction of transcription, and SL1 indicates the SL1 trans-spliced leader. Panel B shows an amino-acid sequence alignment of MOD-5 CeSERT (SEQ ID NO:5) with human SERT (hSERT) (SEQ ID NO:10) and *Drosophila melanogaster* SERT (dSERT) (SEQ ID NO:11). The 12 predicted transmembrane regions are underlined. Amino acids conserved between MOD-5 and at least one of the two other proteins are shown in black boxes, and the two mod-5 point mutations are indicated. mod-5(n822) is a T-to-A transversion mutation resulting in a C225opal nonsense substitution, and mod-5(n823) is a C-to-T transition mutation resulting in a P569S missense substitution. The "▼" indicates potential PKA or PKC phosphorylation sites. The "*" indicates potential N-linked glycosylation sites (consensus N-x-S/T). The "♦" indicates the aspartate residue conserved in SERTs, NETs (norepinephrine transporters), and DATs (dopamine transporters).

We generated an eight kilobase (kb) polymerase chain reaction (PCR) product from the genomic region spanning the first eight exons of Y54E10A__154.A (FIG. 3A) and encoding the first 507 amino acids of the corresponding predicted protein. This construct robustly rescued the serotonin hypersensitivity phenotype of mod-5(n823) mutants in 16 of 20 transgenic lines tested. We obtained a partial cDNA clone of Y54E10A__154.A using reverse transcriptase-PCR (RT-PCR) and determined the 5' and 3' ends of the cDNA using 5'- and 3'-rapid amplification of cDNA ends (RACE), respectively. The 5' end of the cDNA contained an SL1 trans-spliced leader, which is found at the 5' ends of many *C. elegans* transcripts (Krause and Hirsh, *Cell* 49:753–761, 1987). The 3' end contained a poly-A stretch, indicating that we had determined the complete Y54E10A__154.A transcriptional unit (FIG. 3A). This cDNA was capable of rescuing the serotonin hypersensitivity of mod-5 mutants (see below).

Protein sequence comparisons revealed that the predicted protein encoded by our full-length cDNA is 44% identical to human SERT (hSERT; Ramamoorthy et al., 1993) and 45% identical to the other known invertebrate SERT, from *Drosophila melanogaster* (dSERT; Corey et al. *Proc Natl Acad Sci USA* 91:1188–1192, 1994), which is itself 51% identical to hSERT (FIG. 3B). We identified single-base mutations in the Y54E10A__154.A coding sequence in mod-5(n822) and mod-5(n823) mutants (FIG. 3B). The mutation in mod-5 (n822) is predicted to change cysteine 225 (codon TGT) to an opal stop codon (TGA). The mutation in mod-5(n823) is predicted to change proline 569 (CCG) to serine (TCG) within a transmembrane region. We concluded that Y54E10A__154.A is mod-5.

Like SERTs from other species (Barker and Blakely, *Methods Enzymol* 296:475–498, 1998), the MOD-5 protein is predicted to contain 12 putative transmembrane regions (FIG. 3B). Much of the sequence conservation is clustered in or around these transmembrane regions, suggesting that the membrane topology of the SERTs is important for their function. At position 119 of SEQ ID NO:5 (FIG. 3B, diamond), within the first predicted transmembrane domain, MOD-5 has an aspartate residue that is conserved in serotonin, dopamine, and norepinephrine (NE) reuptake transporters but not in gamma-aminobutyric acid (GABA) reuptake transporters (Barker and Blakely, *Methods Enzymol* 296:475–498, 1998). This aspartate may be involved in binding to the amino group in serotonin, dopamine, and NE (Kitayama et al., *Proc Natl Acad Sci USA* 89:7782–7785, 1992). MOD-5 also has other similarities to hSERT and dSERT (FIG. 3B legend).

Both wild-type and mutant CeSERT cDNAs have been obtained and the cDNA sequences of wild-type CeSERT (SEQ ID NO:1), CeSERT(n822) (SEQ ID NO:2), CeSERT (n823) (SEQ ID NO:3), and CeSERT(n3314) (SEQ ID NO:4) as well as the amino acid sequences encoded by wild-type CeSERT (SEQ ID NO:5), CeSERT(n822) (SEQ ID NO:6), CeSERT (n823) (SEQ ID NO:7), and CeSERT (n3314) (SEQ ID NO:8) were identified.

Mod-5(n3314) is a Null Allele

Figure 2A:
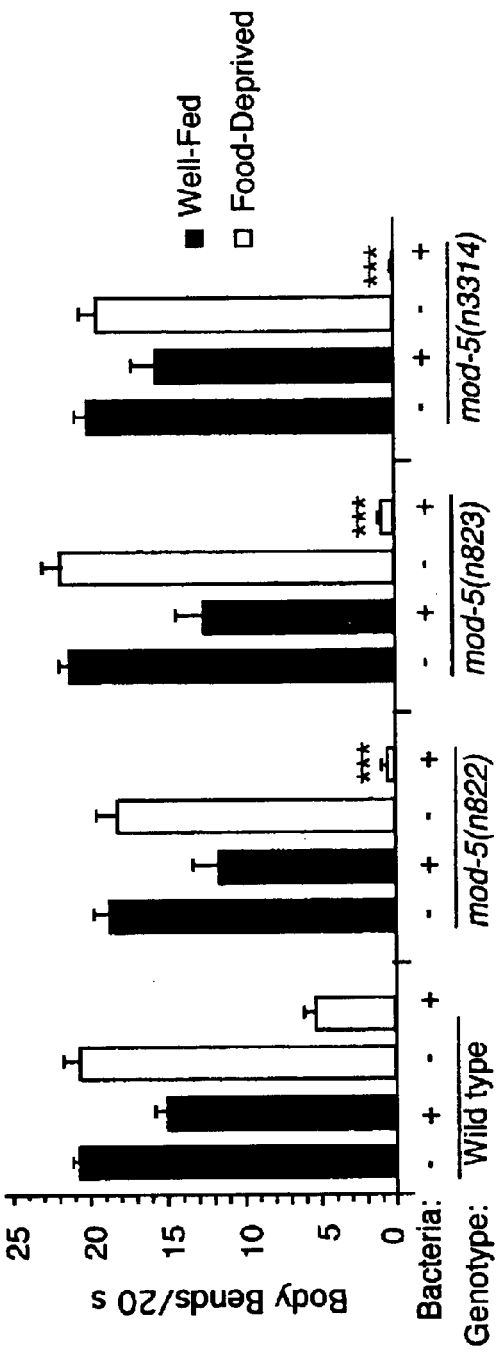
FIG. 2 shows the phenotypic characterization and cloning of mod-5. Panel A indicates that mod-5 mutants exhibited a hyperenhanced slowing response. Data from well-fed (black bars) and food-deprived (gray bars) animals are shown. Panel B shows that the hyperenhanced slowing response exhibited by mod-5(n823) mutants was suppressed by ablation of the NSMs. Panel C indicates that the decrease in endogenous serotonin partially suppressed the mod-5 phenotype. mod-5(n823); cat-4 double mutants displayed an enhanced slowing response intermediate to that of mod-5 (n823) (see FIG. 2A) and cat-4 mutants. Panel D shows that mod-5 mutants were hypersensitive to exogenous serotonin. In panels A–D, the error bars indicate the standard error of the sample mean and the asterisks indicate a p<0.0001 calculated using the Student's t-test.
Figure 2C:
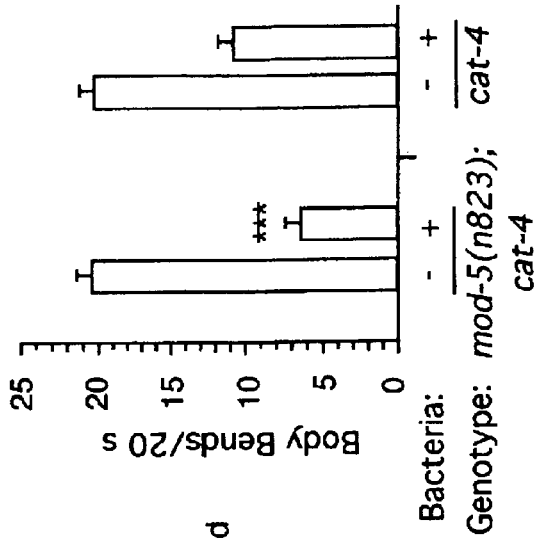

To determine the phenotypic consequence of completely eliminating mod-5 function, we screened libraries of mutagenized animals using PCR to identify large deletions (Jansen et al., Nat Genet 17:119–121, 1997) in the mod-5 genomic locus. We isolated a deletion allele, n3314 that contains a 1688 base pair (bp) deletion in the mod-5 genomic locus (FIG. 3A). The altered open reading frame (ORF) is predicted to encode the first 42 amino acids of MOD-5 and, if the end of exon 2 splices onto the next available splice-acceptor site at the start of exon 8, an additional 18 out-of-frame amino acids before ending at a premature stop codon.

n3314 displayed and failed to complement mod-5(n822) and mod-5(n823) for both the hyperenhanced slowing response and serotonin hypersensitivity in the liquid swimming assay, confirming that n3314 is an allele of mod-5. mod-5(n3314) mutants were more hypersensitive to serotonin than were mod-5(n822) and mod-5(n823) mutants (FIG. 2D). mod-5(n3314) mutants also exhibited a more severe hyperenhanced slowing response than did the nonsense mod-5(n822) and the missense mod-5(n823) mutants (FIG. 2A). On Petri plates without bacteria, the locomotory rate of mod-5(n3314) mutants was not different from that of the wild-type (FIG. 2A).

Well-fed mod-5(n3314) mutants showed no defect in their basal slowing response to bacteria (FIG. 2A). Given the stronger behavioral defects of mod-5(n3314) mutants and the molecular nature of the n3314 deletion, we believe that n3314 is a null allele of mod-5 and that both mod-5(n822) and mod-5(n823) are partial loss-of-function alleles. mod-5(n822), which is predicted to encode only the first 224 amino acids of MOD-5, is not a null allele, based on comparisons of the phenotypes of mod-5(n822), mod-5 (n3314), and mod-5(n822)/mod-5(n3314) transheterozygous animals (FIGS. 2A and D). This activity of mod-5(n822) might be a consequence of the presence of functional mod-5 transcripts produced by alternative splicing or read-through of the stop codon. Alternatively, it is conceivable that the first 224 amino acids of MOD-5 retain partial SERT function. This latter possibility is consistent with our rescue of the serotonin hypersensitivity of mod-5 (n823) mutants with a construct that encodes only the first 507 amino acids of MOD-5, suggesting that all 671 amino acids of MOD-5 are not essential for at least some aspects of SERT function.

Since we had isolated the mod-5 cDNA using RT-PCR and RACE, we sought to confirm that the protein encoded by this cDNA could function in vivo. We constructed a minigene in which the mod-5 cDNA was placed under the control of 2.7 kb of genomic DNA upstream to the first predicted methionine of mod-5. mod-5(n3314) animals transgenic for extrachromosomal arrays consisting of this mini-gene construct were no longer serotonin hypersensitive, confirming that we had defined a functional mod-5 gene and that the mod-5 cDNA could encode a functional SERT and was suitable for serotonin-uptake assays in a heterologous system (see below).

Test for CeSERT Association with Locomotion in C. elegans

C. elegans, for example hemaphrodites, respond to the presence of a bacterial lawn (their food source) by slowing their rate of locomotion. Animals deprived of bacteria for 30 minutes exhibit enhanced slowing when they encounter a bacterial lawn. Genetic, pharmacological, and laser ablation studies demonstrate that this modulatory response is mediated, in part, by serotonin.

Since n822 and n823 mutants were defective in serotonin uptake, we sought to determine if these mutants were abnormal in their responses to endogenous serotonin release. We tested the serotonin-dependent enhanced slowing response (Sawin et al., Neuron 26:619–623, 2000) of these mutants. Whereas well-fed wild-type animals slow their locomotory rate slightly in response to bacteria (the basal slowing response) food-deprived wild-type animals display a greater degree of slowing of locomotory rate in response to bacteria (the enhanced slowing response) (Sawin et al., Neuron 26:619–623, 2000; and FIG. 2A). Strikingly, n822 and n823 mutants exhibited a hyperenhanced slowing response. On Petri plates with bacteria, the locomotory rates of food-deprived n822 and n823 mutants slowed significantly more than did those of food-deprived wild-type animals (FIG. 2A, gray bars). In contrast, on Petri plates without bacteria, the locomotory rates of food-deprived n822 and n823 mutants were not significantly different from those of food-deprived wild-type animals (FIG. 2A, gray bars). Well-fed n822 and n823 mutants exhibited no defect in the serotonin-independent dopanine-dependent basal slowing response to bacteria (FIG. 2A, black bars) (Sawin et al., Neuron 26:619–623, 2000). Genes involved in the enhanced slowing response are called mod (modulation of locomotion defective) (Sawin et al., Neuron 26:619–623, 2000), and we named the gene defined by the allelic mutations n822 and n823 mod-5. The hyperenhanced slowing responses of these mod-5 mutants were presumably a consequence of a defect in the clearing of serotonin from the relevant synapses by uptake into serotonergic neurons, thereby leading to increased serotonin signaling and a greater inhibition of locomotion.

Figure 2B:
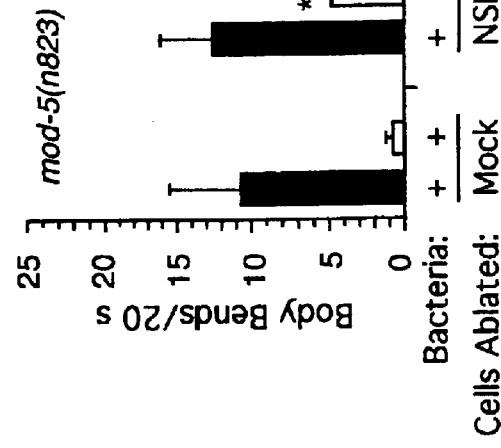
Figure 2D:
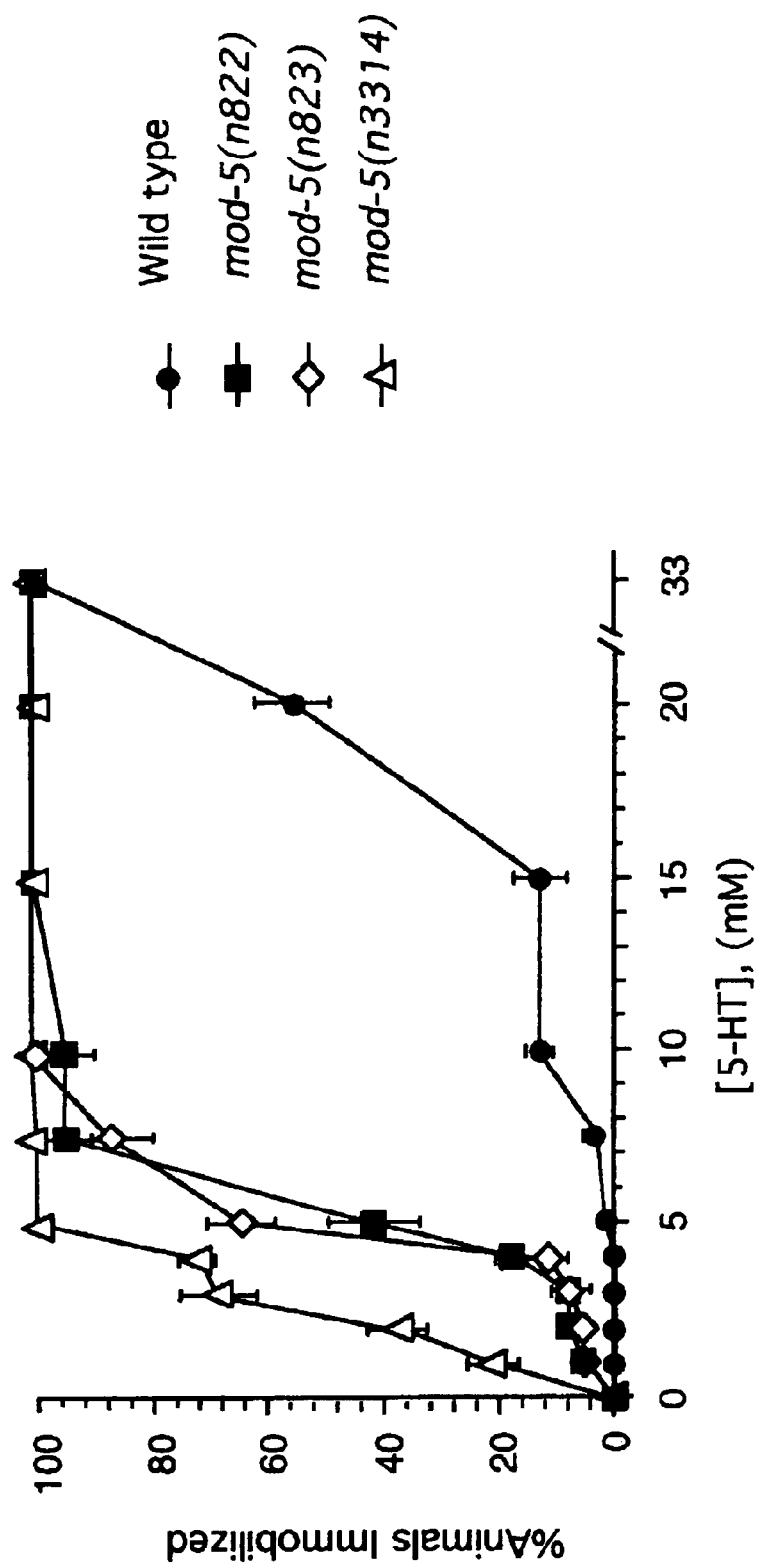

Ablation of the Serotonergic NSMs or a Decrease in Endogenous Serotonin Suppresses mod-5 Mutations Ablation of the serotonergic NSMs with a laser microbeam leads to a defect in the enhanced slowing response (Sawin et al., Neuron 26:619–623, 2000). Since the NSMs were defective in serotonin uptake in mod-5 mutants (see above), we tested whether ablation of the NSMs affected the hyperenhanced slowing response of mod-5 mutants. On Petri plates with bacteria, food-deprived NSM-ablated mod-5(n823) mutants exhibited an enhanced slowing response that was significantly reduced in comparison to that of food-deprived mock-ablated mod-5(n823) mutants (FIG. 2B, gray bars). Well-fed NSM-ablated mod-5(n823) mutants were not significantly affected in their basal slowing response to bacteria (FIG. 2B, black bars). Ablation of the 15 neuron, another pharyngeal neuron, had no effect on the enhanced slowing response of mod-5 mutants, indicating that the effect of the NSM-ablations was not a consequence of the ablation protocol per se.

We reasoned that the ablation of the NSMs probably led to a loss of serotonin needed for the hyperenhanced slowing exhibited by mod-5 mutants. To test this hypothesis, we investigated whether cat-4 mutants, which have decreased serotonin levels (see above), could suppress the mod-5 phenotype. cat-4 mutants are defective in the enhanced slowing response (Sawin et al., Neuron 26:619–623, 2000; and FIG. 2C), and the reduced serotonin in these mutants is the cause of this defect (Sawin et al., Neuron 26:619–623, 2000).

On Petri plates with bacteria, the locomotory rate of food-deprived mod-5(n823); cat-4 double mutants was significantly faster than that of food-deprived mod-5(n823) mutants (compare FIG. 2C to FIG. 2A gray bars), but similar to that of NSM-ablated mod-5(n823) mutants (FIG. 2B), suggesting that for the enhanced slowing response the ablation of the NSMs is equivalent to a reduction in serotonin levels in the animal. That the locomotory rate of food-deprived mod-5(n823); cat-4 double mutants was significantly slower than that of cat-4 mutants (FIG. 2C) is likely a consequence of the effect of residual serotonin in cat-4 mutants (FIG. 1B).

Exogenous serotonin inhibits wild-type C. elegans locomotion (Horvitz et al., Science 216:1012–1014, 1982). To determine if mod-5(n822) and mod-5(n823) mutants were abnormal in their response to exogenous serotonin, we used a liquid swimming assay (Ranganathan et al., Nature 408:470–475, 2000). In this assay, mod-5(n822) and mod-5(n823) mutants were hypersensitive to exogenously added serotonin (FIG. 2D), presumably because this serotonin was not efficiently cleared from the relevant synapses.

MOD-5 Functions as a SERT in Mammalian Cells

Using retroviral-mediated gene transfer (see Example 6), we generated human embryonic kidney 293 (HEK293) cell lines that stably expressed MOD-5. Using these cell lines, we performed uptake assays similar to those previously done for other SERTs (Ramamoorthy et al., Proc Natl Acad Sci USA 90:2542–2546, 1993; Demchyshyn et al., Proc Natl Acad Sci USA 91:5158–5162, 1994). The uptake of [$^3$H] serotonin by MOD-5-expressing cell lines was saturable, indicating that the accumulation of [$^3$H]serotonin in the cells was facilitated by MOD-5 (FIG. 4A). MOD-5-mediated [$^3$H]serotonin transport was strictly dependent on Na$^+$ ions (FIG. 4B), as has been observed for serotonin transport by hSERT (Ramamoorthy et al., Proc Natl Acad Sci USA 90:2542–2546, 1993), rat SERT (rSERT; Blakely et al., Nature 354:66–70, 1991; Hoffman et al., Science 254:579–580, 1991), and dSERT (Demchyshyn et al., Proc Natl Acad Sci USA 91:5158–5162, 1994). By contrast, MOD-5 did not display a strict dependence on Cl$^-$ ions (FIG. 4B), whereas both hSERT and rSERT, but not dSERT, do display such strict dependence (Blakely et al., Nature 354:66–70, 1991; Hoffman et al., Science 254:579–580, 1991; Ramamoorthy et al., Proc Natl Acad Sci USA 90:2542–2546, 1993; Demchyshyn et al., Proc Natl Acad Sci USA 91:5158–5162, 1994).

MOD-5-mediated [$^3$H]serotonin transport occurred in a concentration-dependent and saturable manner (FIG. 4C), with a $K_m$=150±8 nM, a value similar to those reported for other SER s ($K_m$ range=280–630 nM) (Blakely et al., Nature 354:66–70, 1991; Hoffman et al., Science 254:579–580, 1991; Ramamoorthy et al., Proc Natl Acad Sci USA 90:2542–2546, 1993; Corey et al., Proc Natl Acad Sci USA 91:1188–1192, 1994; Demchyshyn et al., Proc Natl Acad Sci USA 91:5158–5162, 1994; Chang et al., Biochem Pharmacol 22:3099–3108, 1996; Padbury et al., Brain Res Mol Brain Res 45:163–168, 1997; Chen et al., Am J Physiol 275:G433–448, 1998; Mortensen et al., Brain Res Mol Brain Res 71:120–126, 1999).

We tested the specificity of MOD-5 by assaying the ability of MOD-5 to transport various radiolabeled neurotransmitters besides serotonin. MOD-5-mediated uptake was highly specific for [$^3$H]serotonin and inefficient at translocating radiolabeled GABA, glutamate, glycine, NE, histamine, and dopamine (FIG. 4D). We also tested the ability of these neurotransmitters to inhibit [$^3$H]serotonin uptake via MOD-5. None of the six neurotransmitters tested, even when present at 100 µM, substantially inhibited the uptake of 50 nM serotonin. We also tested whether octopamine or tyramine, two invertebrate-specific neurotransmitters, could inhibit [$^3$H]serotonin transport; we could not test MOD-5-mediated uptake of these neurotransmitters, as radiolabeled octopamine and tyramine are not available. Tyramine (100 µM) partially inhibited (54%±10% of control) the transport of [$^3$H]serotonin (50 nM) by MOD-5; octopamine (100 µM) did not inhibit (86%±12% of control) MOD-5-mediated [$^3$H]serotonin (50 nM) transport. By comparison, dSERT-mediated transport of 100 nM [$^3$H]serotonin was reduced to 95%±15% of control by 200 µM tyramine and to 82%±15% of control by 200 µM octopamine (Corey et al., Proc Natl Acad Sci USA 91:1188–1192, 1994). These data suggested that there are subtle differences in the properties of MOD-5 and dSERT.

We tested whether MOD-5-mediated [$^3$H]serotonin transport was inhibited by tricyclic antidepressants, SSRIs, and non-specific monoamine transporter inhibitors (Blakely et al., Nature 354:66–70, 1991; Ramamoorthy et al., Proc Natl Acad Sci USA 90:2542–2546, 1993; Demchyshyn et al., Proc Natl Acad Sci USA 91:5158–5162, 1994). The rank order of potency for inhibition of MOD-5-mediated [$^3$H]serotonin transport was imipramine ($K_i$=89±58 nM)≈fluoxetine ($K_i$=133±90 nM)≈paroxetine ($K_i$=179±64 nM)>desipramine ($K_i$=334±115 nM)>citalopram ($K_i$=994±298 nM)>>cocaine ($K_i$=4076±349 nM) (FIG. 4E). This rank order is different from that of other SERTs (for example, the rank order of potency for inhibition of hSERT-mediated [$^3$H]serotonin transport is paroxetine>fluoxetine>imipramine citalopram>>cocaine; Ramamoorthy et al., Proc Natl Acad Sci USA 90:2542–2546, 1993), and for some of the inhibitors the $K_i$ values were higher than those reported for the other SERTs (Blakely et al., Nature 354:66–701991; Hoffman et al., Science 254:579–580, 1991; Ramamoorthy et al., Proc Natl Acad Sci USA 90:2542–2546, 1993; Corey et al., Proc Natl Acad Sci USA 91:1188–1192, 1994; Demchyshyn et al., Proc Natl Acad Sci USA 91:5158–5162, 1994; Chang et al., Brain Res Mol Brain Res 43:185–192, 1996; Padbury et al., Brain Res Mol Brain Res 45:163–168, 1997; Chen et al., Am J Physiol 275:G433–448, 1998; Mortensen et al., Brain Res Mol Brain Res 71:120–126, 1999).

Taken together, the specificity of MOD-5-mediated transport for serotonin, the dependence of such transport on Na$^+$ and Cl$^-$ ions, and the inhibition of serotonin transport by SSRIs establish that MOD-5 is a C. elegans SERT (CeSERT).

MOD-5 is Likely the Only SERT in C. elegans

To determine if MOD-5 is the only SERT in C. elegans, we analyzed the C. elegans genomic sequence for other potentials SERTs and performed in vivo assays of serotonin uptake in mod-5 mutants. We found 15 Na$^+$/Cl$^-$ dependent neurotransmitter transporter-like predicted ORFs in the completed C. elegans genomic sequence (The C. elegans Sequencing Consortium, 1998). Only two of these ORFs, T23G5.5 and T03F7.1, are nearly as similar (43% and 41% identity, respectively) to hSERT as is MOD-5 CeSERT, and only MOD-5 CeSERT and T23G5.5 have an aspartate corresponding to aspartate 119 in MOD-5 CeSERT (SEQ ID NO:5), a conserved residue likely to be functionally important for amine transport (see above). T23G5.5 is a dopamine reuptake transporter and is very inefficient at transporting serotonin (Jayanthi et al., Mol Pharmacol 54:601–609, 1998). Accordingly, from sequence analysis, it is likely that MOD-5 CeSERT is the only SERT in C. elegans. Other species that have been analyzed also contain only one SERT gene.

To determine if a second SERT exists in C. elegans, we tested whether serotonergic neurons in mod-5(n3314)

mutants are be able to take up exogenously added serotonin and whether non-serotonergic cells possess a SERT activity, using anti-serotonin antisera to detect the uptake of serotonin. We used the tph-1 (mg280) mutant, which contains a deletion in the tryptophan hydroxylase gene and is therefore defective in an enzyme essential for serotonin biosynthesis to eliminate endogenous serotonin (Sze et al., *Nature* 403:561–564, 2000). tph-1 mutants completely lack anti-serotonin immunofluorescence (Sze et al., *Nature* 403:561–564, 2000). We have confirmed these findings (Table 1) using the same anti-serotonin antibodies used in FIG. 1B. tph-1 mutants are unlikely to be perturbed in the levels of other biogenic amines since tryptophan hydroxylase only functions in serotonin biosynthesis (Cooper et al., *The Biochemical Basis of Neuropharmacology*, 7th Edition. New York: Oxford University Press, 1996; Sze et al., *Nature* 403:561–564, 2000).

TABLE 1

Fluoxetine phenocopies mod-5 in serotonin uptake assays in vivo
% Serotonin-positive NSMs

| | Pretreatment 1 | | | |
|---|---|---|---|---|
| | | Fluoxetine (mM) | | |
| | No Drug | 0.22 | 0.29 | 0.44 |
| | Pretreatment 2 | | | |
| Genotype | No Drug | 5-HT | 5-HT + Fluoxetine | |
| tph-1 | 0 | 98 | 20 | 7 | 0 |
| mod-5, tph-1 | 0 | 0 | N/A | N/A | N/A |

In pretreatment 1, animals were incubated for 1 hr on plates containing no drug or the specified concentration of fluoxetine. In pretreatment 2, animals from plates with no drug in pretreatment 1 were transferred to plates containing no drug or 2 mM serotonin, and animals from plates with fluoxetine were transferred to plates containing 2 mM serotonin and the same specified concentration of fluoxetine as in pretreatment 1. After 2 hours, animals were fixed and stained with anti-serotonin antisera. N/A stands for not applicable. At least 100 animals were assayed in each condition for each genotype; >200 mod-5, tph-1 animals pretreated with serotonin in pretreatment 2 were scored. The tph-1 (mg280) and mod-5 (n3314) alleles were used.

To identify cells capable of serotonin uptake, we examined the head, ventral cord, gut, and tail of tph-1 mutants pretreated with serotonin and observed serotonin immunofluorescence in only the serotonergic neurons (see below). To examine the requirement of MOD-5 CeSERT for serotonin uptake by serotonergic neurons, we scored the NSMs for serotonin uptake, since these neurons are the most brightly staining serotonergic neurons in the animal following incubation with exogenous serotonin. Without serotonin pretreatment, both tph-1 single and mod-5(n3314); tph-1 double mutants had no NSMs that were serotonin positive (Table 1). In contrast, when pretreated with serotonin, tph-1 mutants displayed robust serotonin staining in the NSMs, while mod-5(n3314); tph-1 double mutants showed none (Table 1). We observed similar results for the serotonergic ADF neurons in the head and for the hermaphrodite-specific neurons (HSNs) in the mid-body. Thus, no other transporter is likely to transport serotonin into serotonergic neurons in the absence of the MOD-5 CeSERT. We also examined the head, ventral cord, gut, and tail of mod-5(n3314); tph-1 double mutants pretreated with serotonin and observed no serotonin immunofluorescence anywhere in the animal, indicating that no other cells display serotonin uptake activity in the absence of MOD-5 CeSERT.

These serotonin uptake experiments taken together with the analysis of the *C. elegans* genomic sequence indicate that MOD-5 is likely to be the only SERT in *C. elegans*.

Mod-5 Interacts Genetically with Mod-1 and Goa-1

Figure 5A:
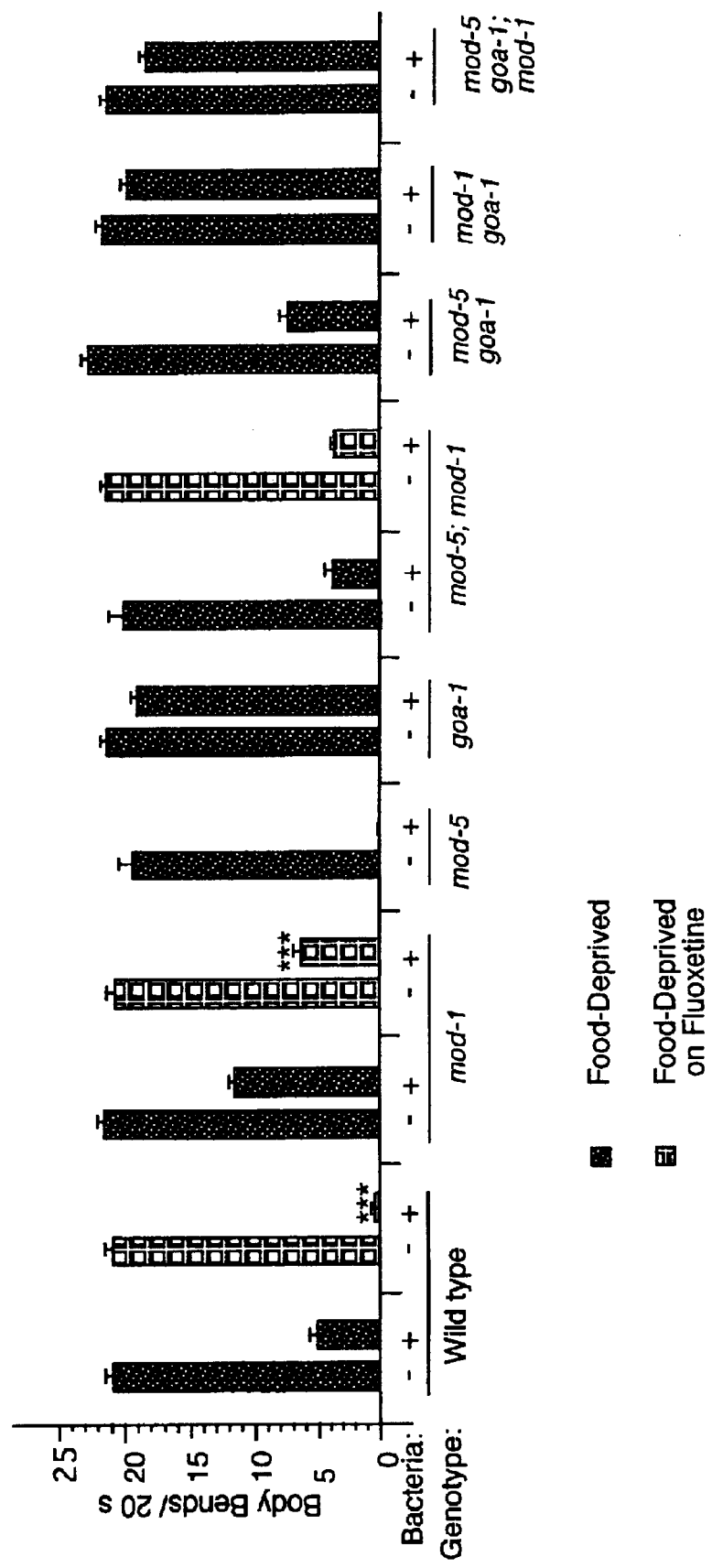
FIG. 5 shows mod-5 genetic interactions and serotonin- and MOD-5 CeSERT-dependence of the potentiating effect of fluoxetine. In Panel A the gray bars show the enhanced slowing response of mod-1, goa-1, mod-5 goa-1, goa-1; mod-1, mod-5; mod-1, and mod-5 goa-1; mod-1 mutants. The hatched bars show the effect of fluoxetine on the enhanced slowing response of wild-type animals (Sawin et al., Neuron 26:619–623, 2000) and mod-1 and mod-5; mod-1 mutants. Panel B shows rescue by serotonin preincubation of the resistance of bas-1; cat-4 mutants to the potentiating effect of fluoxetine on the enhanced slowing response. Panel C shows that mod-5(n3314) mutants retained normal sensitivity to fluoxetine-mediated paralysis. In panels A–C, error bars indicate the standard error of the sample mean and the asterisks indicate a p<0.0001 calculated using the Student's t-test.

Mutants defective in the serotonin-mediated enhanced slowing response defined several mod genes (Sawin et al., *Neuron* 26:619–623, 2000). One of these genes, mod-1, encodes a novel ionotropic serotonin receptor, a serotonin-gated chloride channel (Ranganathan et al., 2000). On Petri plates with bacteria, the locomotory rate of food-deprived mod-1 mutants is substantially faster than that of the wild-type (Sawin et al., *Neuron* 26:619–623, 2000; Ranganathan et al., *Nature* 408:470–475, 2000; also FIG. 5A, gray bars). In comparison, mod-5 mutants exhibit a hyperenhanced slowing response (FIG. 5A).

To define the genetic pathway in which mod-1 and mod-5 act in the enhanced slowing response, we characterized mod-5(n3314); mod-1 (ok103) double mutants. mod-1 (ok103) is a null allele by genetic and molecular criteria (Ranganathan et al., 2000). If the function of the MOD-1 serotonin receptor were essential for the effects of serotonin not cleared from synapses in mod-5 mutants, then eliminating mod-5 function should have had no effect in a mutant that lacked mod-1 function, i.e., mod-5(n3314); mod-1 (ok103) double mutants should exhibit the same phenotype as mod-1 (ok103) single mutants. However, the enhanced slowing response of mod-5(n3314); mod-1 (ok103) double mutants was intermediate to the responses of mod-1 (ok103) and mod-5(n3314) single mutants (FIG. 5A, gray bars). At least five trials were performed for each genotype. This observation indicates that the serotonin signaling triggered by bacteria in the enhanced slowing response acts via at least two parallel serotonin signaling pathways, a MOD-1-dependent pathway and a MOD-1-independent pathway. This observation is also consistent with the observation that mod-1 (ok103) single mutants were not completely defective in the enhanced slowing response (FIG. 5A).

Animals carrying mutations in the G-protein gene goa-1 ($G\alpha_o$, G-protein 0 alpha subunit) (Mendel et al., *Science* 267:1652–1655, 1995; Segalat et al., *Science* 267:1648–1651,1995) are also defective in the enhanced slowing response (Sawin et al., *Neuron* 26:619–623, 2000; also FIG. 5A). Since GOA-1 animals are resistant to serotonin in assays of locomotion (Segalat et al., *Science* 267:1648–1651, 1995; and our observations), pharyngeal pumping (Segalat et al., *Science* 267:1648–1651, 1995), and egg-laying (Mendel et al., *Science* 267:1652–1655, 1995; Segalat et al., *Science* 267:1648–1651, 1995), we tested whether the MOD-1-independent pathway might involve goa-1. As with mod-5; mod-1 double mutants, the enhanced slowing response of mod-5(n3314) goa-1(n1134) double mutants was intermediate to the responses of mod-5(n3314) and goa-1 (n1134) single mutants (FIG. 5A, gray bars), indicating that serotonin signaling triggered by bacteria in the enhanced slowing response does not act solely through goa-1. In comparison, food-deprived mod-5(n3314) goa-1 (n1134); mod-1 (ok103) triple mutants exhibited very little slowing in response to bacteria (FIG. 5A). These observations suggested that MOD-1 and GOA-1 act in two parallel pathways that together mediate the response to the excess serotonin signaling in mod-5(n3314) mutants.

Fluoxetine Blocks Serotonin Uptake in vivo

Since fluoxetine blocked [$^3$H]serotonin transport in mammalian cells expressing MOD-5 CeSERT (see above), we tested whether fluoxetine could block serotonin uptake in vivo in *C. elegans* (Table 1). We pretreated tph-1 mutants with fluoxetine, incubated the animals with serotonin, and scored the number of serotonin-positive NSMs. We observed, for example, few serotonin-positive NSMs when tph-1 mutants were pretreated with 0.22 mM fluoxetine (Table 1), a concentration sufficient to potentiate the enhanced slowing response (see below). Furthermore, tph-1 mutants pretreated with as little as 0.44 mM fluoxetine, a concentration lower than that required for all the MOD-5 CeSERT-independent effects of fluoxetine (see below), were as defective in serotonin uptake as were untreated mod-5 (n3314); tph-1 double mutants (Table 1). These observations indicate that fluoxetine may block serotonin uptake in *C. elegans* in vivo and may do so by inhibiting MOD-5 CeSERT.

The Potentiation of the Enhanced Slowing Response by Fluoxetine Requires MOD-5 CeSERT and Serotonin When wild-type animals that have been food-deprived in the presence of 0.22 mM fluoxetine encounter bacteria, they slow their locomotory rate more than if they had been food-deprived in the absence of fluoxetine (Sawin et al., *Neuron* 26:619–623, 2000; see FIG. 5A). This fluoxetine-mediated potentiation of the enhanced slowing response resembles the hyperenhanced slowing response exhibited by mod-5(n3314) mutants (FIG. 5A), suggesting that fluoxetine causes this potentiation by blocking MOD-5 CeSERT function. Accordingly, mod-5(n3314) mutants should be resistant to the potentiating effect of fluoxetine on the enhanced slowing response. Since food-deprived mod-5(n3314) mutants exhibit an extreme hyperenhanced slowing response that cannot be further potentiated by fluoxetine treatment (FIG. 5A), we used mod-5(n3314); mod-1 (ok103) double mutants to test this hypothesis. These double mutants are partially suppressed for the hyperenhanced slowing response exhibited by mod-5(n3314) animals (FIG. 5A, gray bars), and therefore a potentiation of the enhanced slowing response could be observed.

The enhanced slowing response of mod-1 (ok103) mutants was potentiated by fluoxetine (FIG. 5A, hatched bars), indicating that fluoxetine can potentiate the enhanced slowing response in the absence of MOD-1 serotonin receptor function. This observation was consistent with the phenotype of mod-5(n3314); mod-1 (ok103) double mutants in this assay, which suggested that there are MOD-1-independent serotonin pathways through which the enhanced slowing response is effected. In comparison, mod-5(n3314); mod-1 (ok103) double mutants were completely resistant to the potentiating effect of fluoxetine on the enhanced slowing response (FIG. 5A, hatched bars) (At least ten trials were performed for each genotype.) Consequently, the MOD-5 CeSERT is likely the only in vivo target in *C. elegans* on which fluoxetine acts to potentiate the enhanced slowing response.

Since fluoxetine-mediated potentiation of the enhanced slowing response is MOD-5 CeSERT-dependent, it is also likely to be serotonin-dependent, as we previously suggested (Sawin et al., *Neuron* 26:619–623, 2000), based on the observation that the enhanced slowing response in bas-1 (ad446); cat-4 double mutants (bas: biogenic amine synthesis defective) is resistant to such potentiation. However, our studies of egg-laying by tph-1 mutants indicate that the resistance of cat-4 animals to the effects of high concentrations of fluoxetine likely is not caused by a deficiency in serotonin in these animals (see below). Since tph-1 mutants display sluggish locomotion, they could not be assayed for resistance to the fluoxetine-mediated potentiation of the enhanced slowing response.

We sought to determine if the serotonin-deficiency of bas-1; cat-4 double mutants renders these animals resistant to the potentiating effect of fluoxetine. The defect in the enhanced slowing response of bas-1; cat-4 double mutants in the absence of fluoxetine treatment can be rescued by preincubating the animals on Petri plates containing 2 mM serotonin (Sawin et al., 2000; and FIG. 5B), a pretreatment sufficient for the detection of serotonin in the NSMs of cat-4 (FIG. 1B) and tph-1 (Table 1) mutants. When bas-1; cat-4 mutants were preincubated with serotonin and then food-deprived in the presence of fluoxetine, they exhibited a potentiated enhanced slowing response (FIG. 5B). Consequently, restoration of serotonin to bas-1; cat-4 mutants is sufficient for fluoxetine to potentiate the enhanced slowing response of these mutants. We conclude that the effect of fluoxetine on the enhanced slowing response is dependent not only on MOD-5 CeSERT, but also on serotonin.

Fluoxetine Induces Nose Contraction and Paralysis in Mod-5 and Tph-1 Mutants

Treatment of *C. elegans* with high concentrations (0.25–1 mg/ml; 0.7–2.9 mM) of fluoxetine leads to paralysis (Choy and Thomas, *Mol Cell* 4:143–152, 1999), contraction of nose muscles (Choy and Thomas, *Mol Cell* 4:143–152, 1999), and stimulation of egg-laying (Weinshenker et al., *Neurosci* 15:6975–6985, 1995). The concentrations of fluoxetine required for these effects are at least 2.5 fold higher than that required to detect a block of serotonin uptake in vivo (see above) and for the potentiation of the enhanced slowing response (FIG. 5B and Sawin et al., 2000). (At least five trials were performed for each genotype.)

Figure 5C:
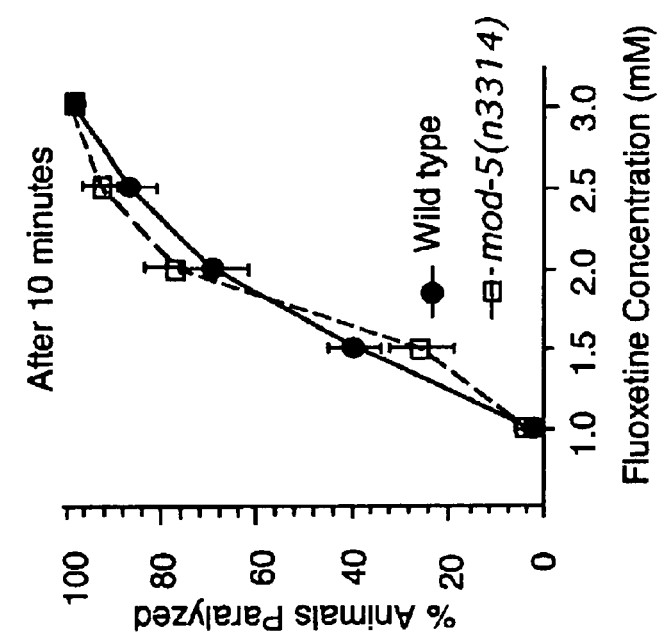
Figure 5B:
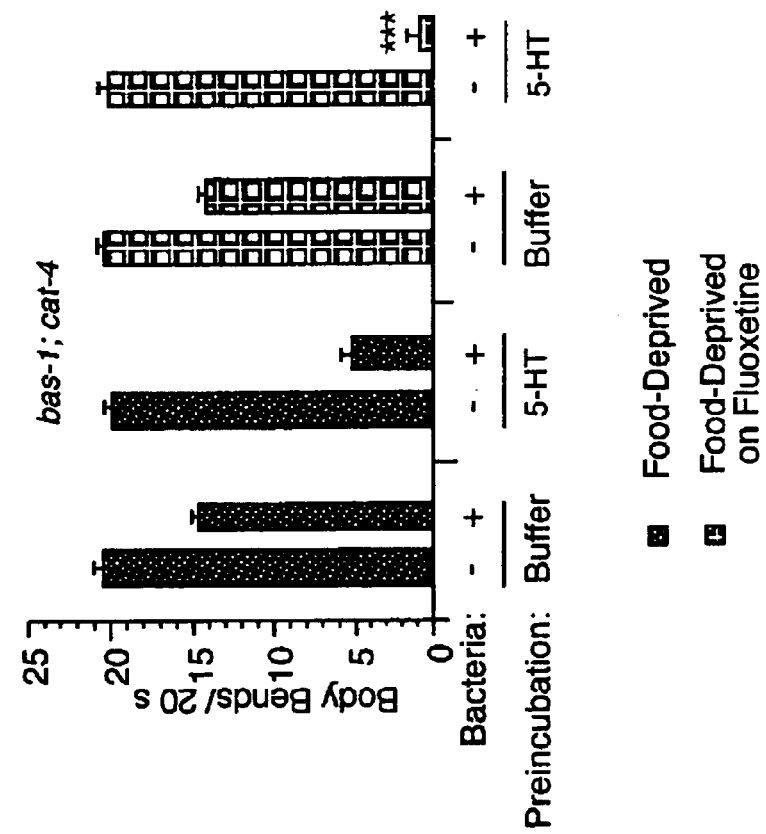

To acertain whether the only in vivo target for fluoxetine is MOD-5 CeSERT, we tested mod-5(n3314) mutants for their responses to high concentrations of fluoxetine. mod-5 (n3314) mutants retained wild-type sensitivity to fluoxetine in assays of paralysis induced by fluoxetine treatment (FIG. 5C). (Five trials with 20 animals of each genotype at each concentration and the animals were scored for paralysis after ten minutes.) There was no difference in the time-course of paralysis at any of the concentrations tested. These observations indicate that fluoxetine-induced paralysis in *C. elegans* is not caused by the lack of serotonin uptake from synapses. Fluoxetine-treated wild-type and mod-5(n3314) mutant animals assumed a rigid body posture. In comparison, serotonin-treated animals assumed a relaxed and flaccid body posture, suggesting that the mechanisms of locomotory inhibition by serotonin and fluoxetine are distinct. Serotonin has been proposed to decrease excitatory input to the locomotory muscles (Nurrish et al., *Neuron* 24:231–242, 1999). Given the two distinct body postures, we show that fluoxetine may directly or indirectly increase excitatory input or decrease inhibitory input to the locomotory muscles.

When treated with fluoxetine for 20 minutes, a similar proportion of wild-type and mod-5(n3314) mutant animals had contracted noses (100% at 2.9 mM, and approximately 25% at 1.5 mM). Thus, the effect of fluoxetine on nose contraction also appears to act via a MOD-5 CeSERT-independent pathway. This conclusion is consistent with the conclusion by Choy and Thomas (1999) that fluoxetine-mediated nose contraction is serotonin-independent, although their hypothesis was based on studies of cat-1 (e1111) mutants, which are defective in signaling by several biogenic amines (Duerr et al., *J Neurosci* 19:72–84, 1999), and cat-4 mutants, which we found to not completely lack serotonin (FIG. 1B).

That the effects of high concentrations of fluoxetine on nose-contraction and paralysis were independent of MOD-5 CeSERT suggested that fluoxetine acts either on another SERT or on a distinct non-SERT target(s). As discussed above, it is likely that MOD-5 is the only SERT in *C. elegans*, making it also likely that a non-SERT target(s) of fluoxetine mediates the MOD-5 CeSERT-independent effects. Such non-SERT targets may or may not be part of a serotonergic signaling pathway. We explored the requirement for serotonin by testing whether fluoxetine can act in animals that lack serotonin. The serotonin-deficient mutants that have been used in numerous prior studies (e.g., Weinshenker et al., *J Neurosci* 15:6975–6985, 1995; Choy and Thomas, *Mol Cell* 4:143–152, 1999; Sawin et al., *Neuron* 26:619–623, 2000), such as cat-1, cat-4, and bas-1 mutants, all affect multiple biogenic amines. None of the mutants have been shown to cause a complete loss of serotonin function. We therefore tested tph-1 mutants, which appear to completely lack serotonin (see above), for their response to fluoxetine.

100% of tph-1 animals displayed contracted noses after treatment with 2.9 mM fluoxetine for 20 minutes. We found that fluoxetine treatment paralyzed tph-1 mutants to a similar extent as wild-type animals, suggesting that paralysis by high concentrations of fluoxetine is also a serotonin-independent process.

Fluoxetine Stimulates Egg-laying in Mod-5 and Tph-1 Mutants

Figure 6D:
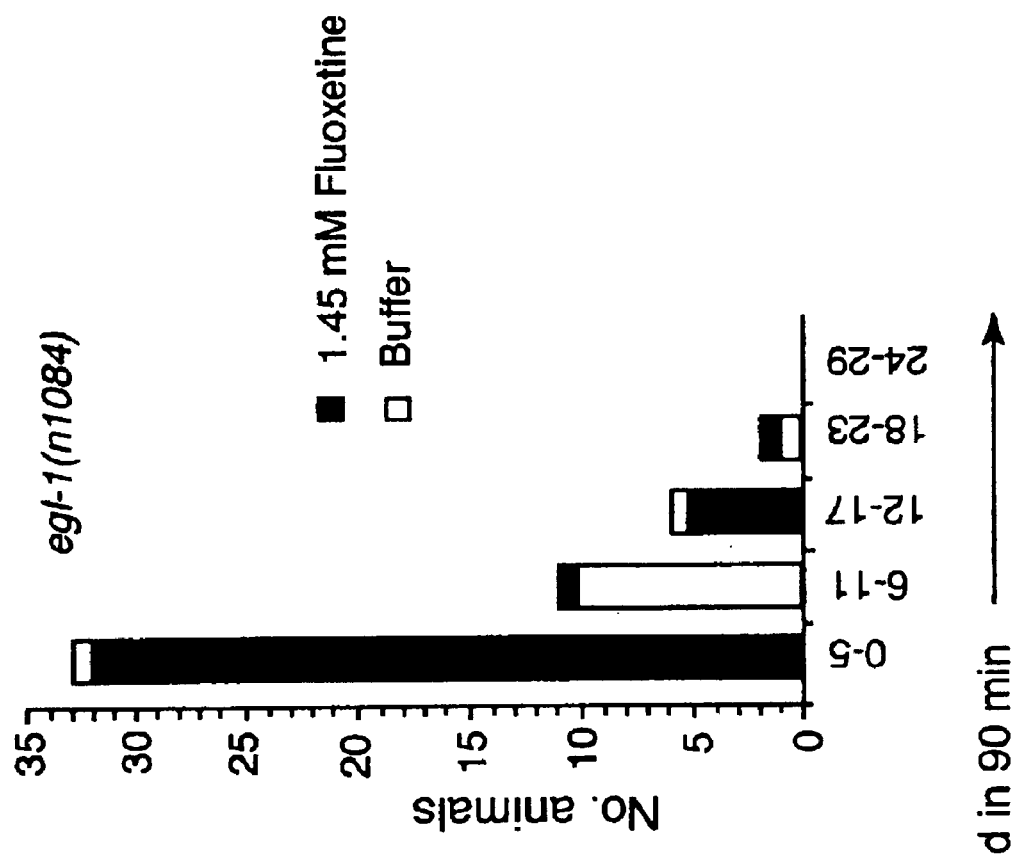
FIG. 6 shows the serotonin- and MOD-5 CeSERT-independence of fluoxetine-induced egg-laying. Fluoxetine-induced egg-laying (n=50 for each genotype) is represented by a bar graph in panel A for wild-type animals, in panel B for mod-5(n3314) mutants, in panel C for tph-1 mutants, in panel D for cat-4 mutants, and in panel E for egl-1 mutants.
Figure 7A:
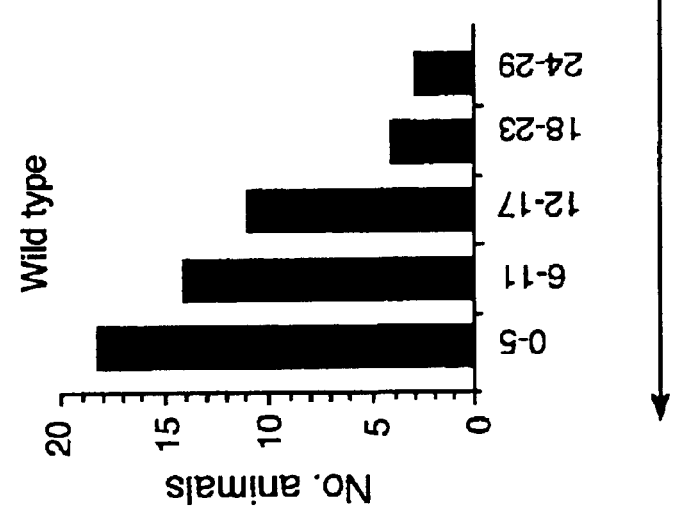
FIG. 7 shows that mod-5(n3314) mutants, but not tph-1 mutants, are hypersensitive to stimulation of egg-laying by serotonin. Serotonin-induced stimulation of egg-laying (n=50 for each genotype) is represented by a bar graph in panel A for wild-type animals, in panel B for mod-5(n3314) mutants, and in panel C for tph-1 mutants.
Figure 7B:
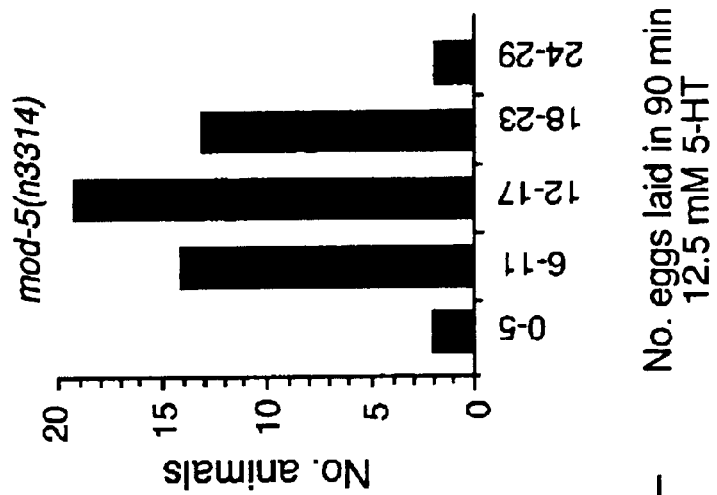

In 1.5 mM fluoxetine, mod-5(n3314) mutants were stimulated to lay eggs to nearly the same extent as was the wild-type (FIGS. 6A and B; black bars), suggesting that fluoxetine can stimulate egg-laying via one or more MOD-5 CeSERT-independent pathways. Nevertheless, mod-5 (n3314) mutants were hypersensitive to exogenous serotonin in assays of egg-laying (FIGS. 7A and B), suggesting that MOD-5 CeSERT can affect serotonergic synapses that regulate egg-laying. mod-5(n3314) mutants and wild-type animals contain similar numbers of eggs (25.7±2.8 and 26.3±2.2, respectively), indicating that this hypersensitivity to exogenous serotonin was not a consequence of differences in basal egg-laying rates between wild-type animals and mod-5 mutants but rather a result of excess serotonin signaling in mod-5(n3314) mutants.

Given that the stimulation of egg-laying by fluoxetine did not require the MOD-5 CeSERT, we investigated whether this stimulation required serotonin. tph-1 mutants were partially resistant to the stimulation of egg-laying by fluoxetine (FIGS. 6A and C) indicating that serotonin mediated some but not all of the egg-laying response to fluoxetine. In contrast, cat-4 mutants were completely resistant to fluoxetine-induced egg-laying (FIGS. 6A and D), as reported by Weinshenker et al. (1995).

Figure 7C:
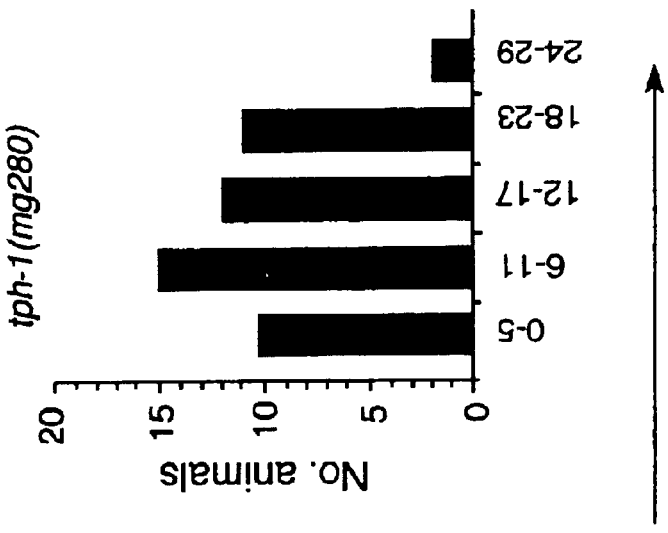

The reduction in egg-laying by tph-1 mutants in response to fluoxetine (FIG. 6C) is unlikely to be caused by a lower number of eggs within tph-1 mutants or the inability of egg-laying muscles in tph-1 mutants to respond to stimulatory input: tph-1 mutants contain more eggs than do wild-type animals (Sze et al., 2000) and tph-1 mutants laid about the same number of eggs in response to exogenous serotonin as did wild-type animals (FIG. 7C). That mod-5(n3314) and tph-1 mutants laid a significant numbers of eggs in response to fluoxetine argues that the mechanism(s) through which fluoxetine stimulates egg-laying in *C. elegans* is not only MOD-5 CeSERT-independent, but also, in part, serotonin-independent.

Figure 6E:
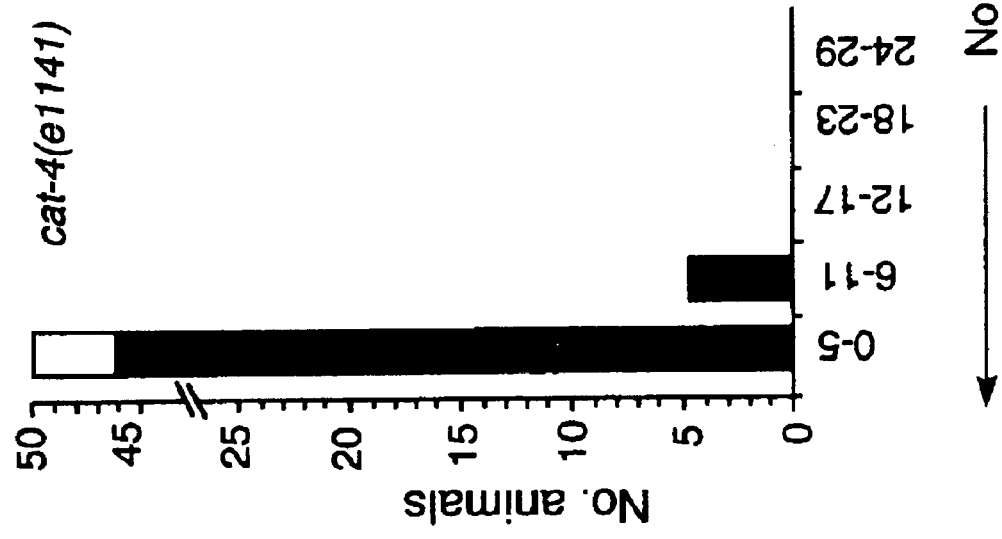

The serotonergic HSN motor neurons innervate the egg-laying muscles and drive egg-laying (Trent et al., *Genetics* 104:619–647, 1983; Desai et al., *Nature* 336:638–646, 1988). egl-1(n1084) mutants, which lack the HSNs (Desai et al., *Nature* 336:638–646,1988), released some eggs in the absence of fluoxetine (FIG. 6E, gray bars), presumably because these animals were severely bloated with eggs. However, treatment with fluoxetine had no effect on egg-laying in egl-1 mutants (FIG. 6E, black bars). These observations indicate that the HSNs are required for the stimulation of egg-laying by fluoxetine.

Figure 8A:
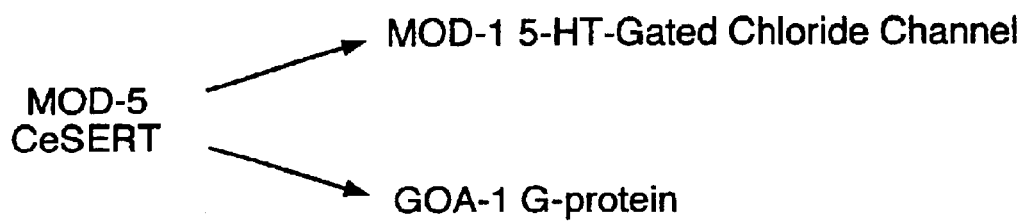
FIG. 8 shows non-limiting models for the effects of fluoxetine on *C. elegans* behaviors. Panel A shows that MOD-5 CeSERT acts upstream of the MOD-1 serotonin-gated chloride channel and the GOA-1 G-protein. Panel B diagrams the potentiating effect of low concentrations of fluoxetine on the enhanced slowing response is serotonin- and MOD-5 CeSERT-dependent. 5-HTR is a metabotropic serotonin receptor that GOA-1 may couple to. The "▶" represents serotonin and the "●" represents chloride ions. Panel C shows that the effects of high concentrations of fluoxetine on egg-laying, nose contraction and paralysis are MOD-5 CeSERT-independent. High concentrations of fluoxetine act on non-SERT targets and on a non-serotonin pathway to paralyze *C. elegans* and to lead to the contraction of nose muscles. By contrast, stimulation of egg-laying by fluoxetine is MOD-5 CeSERT-independent but still partially dependent on serotonin.
Figure 8B:
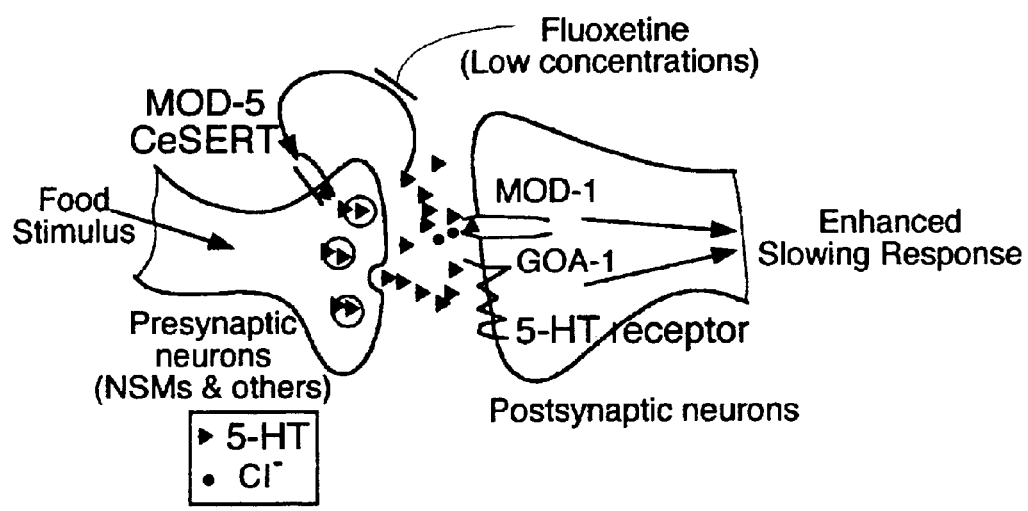
Figure 8C:
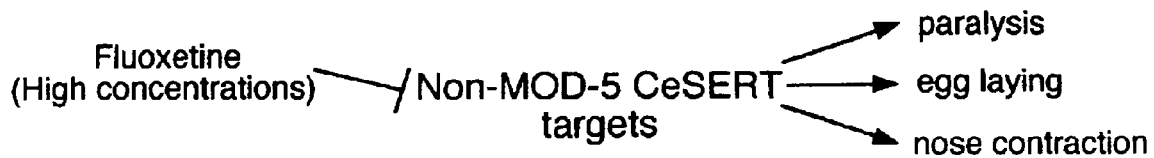

The present invention provides non-limiting models showing a possible pathway of MOD-5 function and showing the likely effects of fluoxetine on *C. elegans* behaviors (FIGS. 8A–C). However, other models are not excluded from the invention.

Related CeSERT Polypeptides

In addition to the polypeptides described above, the invention includes any protein that is substantially identical to the CeSERT polypeptides of SEQ ID NOS:5–8; such homologs include other substantially pure naturally-occurring *C. elegans* proteins as well as allelic variants; natural mutants; induced mutants; DNA sequences that encode CeSERT proteins and also hybridize to CeSERT DNA sequences under high stringency conditions or, less preferably, under low stringency conditions (e.g., washing at 2×SSC at 40° C. with a probe length of at least 40 nucleotides); and proteins specifically bound by antisera directed to a CeSERT polypeptide. The invention also includes chimeric polypeptides that contain a portion of a CeSERT polypeptide.

Furthermore, the invention includes analogs of any of the naturally-occurring polypeptides described herein. Analogs can differ from the naturally-occurring protein by amino acid sequence differences, by post-translational modifications, or by both. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptide by alterations in primary sequence. These include degenerate variants, both natural and induced (for example, resulting from random mutagenesis by irradiation or exposure to ethanemethylsulfate or by site-specific mutagenesis, as described in Sambrook, Fritsch and Maniatis, *Molecular Cloning: A Laboratory Manual* (2d ed.), Cold Spring Harbor Press, 1989, or Ausubel et al., *Current Protocols in Molecular Biology*, John Wiley & Sons, New York, N.Y., 1994). Also included are cyclized peptides, molecules, and analogs that contain residues other than L-amino acids (e.g., D-amino acids) or non-naturally occurring or synthetic amino acids (e.g., β or γ amino acids).

In addition to full-length polypeptides, the invention also includes polypeptide fragments. Fragments of polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a CeSERT nucleic acid or amino acid sequence in a sample to be assayed.

Screening Systems for Identifying Therapeutic Agents

Based on our experimental results, we have developed a number of screening procedures for identifying compounds that modulate the biological activity of a serotonin reuptake transporter. These compounds may be used as therapeutic agents (e.g., pharmaceuticals to treat or prevent disorders associated with serotonin-mediated cellular responses), or may be leads for such compounds, and can be used in human patients. In particular examples, these compounds specifically decrease or increase serotonin reuptake transporter biological activity, such as the biological activity of CeSERT or its human homolog hSERT. Also useful in the invention are compounds that specifically affect serotonin receptors and/or a serotonin-gated ion channel. In general, the screening methods of the invention involve screening any number of compounds for therapeutically active agents by employing various in vitro or in vivo experimental systems. These screens may be carried out in a nematode expressing either a wild-type or mutant CeSERT gene, or expressing a truncated CeSERT polypeptide that functions like a wild-type CeSERT polypeptide. These screens may also be carried out in the presence or absence of a compound that affects the serotonergic pathway in C. elegans or other animals, for example, humans.

The CeSERT genes, polypeptides, and strains of the present invention may be used in drug design methods. For example, wild-type CeSERT has a pharmacology that is distinct from other existing SERTs, and these pharmacological characteristics may represent clues as to how drugs that affect SERT function mediate their effects. Sequence comparisons between hSERT and CeSERT reveal the regions of the polypeptides that lead to the differential pharmacology. The information obtained from this analysis will lead to the targeted development of therapeutic compounds that are specific in their effects on hSERT.

In addition, the CeSERT point mutations of the present invention, with a partial loss of CeSERT gene function, may identify specific amino acid residues that are important for maximal SERT function. Therapeutic compounds aimed at these sites, or aimed at avoiding these sites, may lead to the modification of existing therapeutic agents or the development of new therapeutic agents.

Furthermore, the truncated CeSERT polypeptide of the present invention, that still maintains wild-type CeSERT activity, may also be useful in identifying or designing SERT modulatory compounds. For example, the truncated CeSERT of the present invention encodes only two-thirds of the wild-type CeSERT polypeptide, yet maintains CeSERT polypeptide activity. This truncated CeSERT, or any other CeSERT polypeptide that has been further truncated, yet still maintains wild-type polypeptide activity, may be used as a target for rational drug design. A therapeutic compound designed using the truncated CeSERT polypeptide may be more efficacious than one designed using the full-length polypeptide as a target, because the truncated polypeptide is a better-defined target. For example, a therapeutic compound that modulates the function of a truncated SERT may modulate the endogenous (full-length) SERT better than a drug that was originally selected to target the full-length SERT, or may have fewer side effects because it may not bind to other portions of the full-length SERT.

The CeSERT genes, polypeptides, and strains of the present invention may also be used to screen for new drugs that modulate SERT activity. With the knowledge of the present invention that wild-type C. elegans have an endogenous SERT and that C. elegans with mutated CeSERT genes have specific phenotypes, therapeutic drug screens may be carried out in C. elegans, assaying their behaviors. These in vivo screens for compounds that modulate SERT function are different from the in vitro screens that have been done to date and that have resulted in the identification of therapeutic agents that are currently available on the market.

In the same screening methods of the present invention, the SERT is in its native biological context and interacts with other components of the serotonin pathway in a normal way. In such an in vivo setting, a high-throughput drug screen can generate an entirely new class of lead compounds that directly affect the function of SERTs, including an hSERT. In addition, such an in vivo screen provides access to the entire pathway of molecules that interface with SERT. Therefore, such screening methods may identify completely new classes of drugs whose immediate target is not SERT, but rather a molecule that is upstream of SERT.

The present invention also provides methods for identifying compounds that have few or no side effects. Side effects of drugs arise as a consequence of complex interactions of a compound with the entire biological system of the human body. For this reason, a lead compound with excellent promise in an in vitro assay may be found to be unsuitable after testing in humans or other animals.

C. elegans is an appropriate model for gaining an understanding of the range of a drug's effects in an animal model system. C. elegans systems are currently being used for screening for therapeutic agents with relevance to human diseases, and many clinically used compounds, particularly those that perturb serotonin neurotransmission, affect C. elegans in a biologically relevant and tractable manner.

The C. elegans strains of the present invention, with little or no SERT function, may be used to assay the effects of therapeutic compounds at an in vivo level in a variety of ways. Existing drugs, including serotonin selective reuptake inhibitors, for example, fluoxetine, sertraline, paroxatine; monoamine oxidase inhibitors, and other antidepressants, including citalopram, may be tested for side effects using the methods of the present invention. In addition, migraine medications, for example, sumatriptan and rizatriptan, and anti-emetics, such as granisetron and ondansetron, may also be assayed for their side effects. While much is known about the mechanism of action of such therapeutic compounds, very little is known regarding the side effects of these compounds. In addition, compounds that counteract these side effects may also be tested.

As an example of how the C. elegans strains of the present invention may be used to assay the effects of therapeutic compounds in an in vivo setting, compounds identified to modulate SERT may be evaluated for their SERT-independent effects (side effects) by administering the compound to C. elegans carrying a mutation in CeSERT that reduces or eliminates SERT function. A compound that has no effect on a C. elegans strain with a deletion in the CeSERT gene is likely to have fewer side effects than a compound that has an effect on a strain carrying a deletion in the CeSERT gene. Examples of SERT-independent effects or side effects include altered locomotion, pharyngeal pumping, egg-laying, nose contraction, and defecation behaviors.

If a compound does have an effect on a strain carrying a deletion in CeSERT, that phenotype can then be used to identify and clone the genes in C. elegans that encode the secondary targets. Cloning of these secondary targets, in turn, can lead to the identification of molecules in humans that are responsible for the side effects caused by drugs that modulate SERT function.

In addition, the methods, genes, and strains of the present invention can be used to identify compounds that modulate hSERT function. Transgenic C. elegans strains that contain a deletion in the CeSERT gene and express a wild-type hSERT polypeptide can be utilized in high-throughput screens to identify agonists and antagonists of human SERT. Compounds that may be tested include ones that are untested for their ability to modulate serotonin neurotransmission, as well as chemically modified derivatives of known compounds that modulate SERT. Such compounds may be more efficacious than the known compounds. Screens, such as these should yield compounds that may be used as therapeutic agents for humans, especially since the compounds are identified through in vivo assays, wherein hSERT approximates its function in humans far better than what can be achieved through in vitro assays.

In addition, a screening system involving transgenic C. elegans strains that contain a deletion in the CeSERT gene and express a wild-type hSERT polypeptide can be used to identify compounds that interface indirectly with hSERT function. For example, if an endogenous kinase is required for turning on hSERT function, then an inhibitor of such a kinase would result in lower SERT function. Such a result would be manifested in the same manner as a direct serotonin reuptake inhibitor. However, the mechanisms of regulation through the kinase could yield vastly different kinetics and/or magnitudes in hSERT function. It is quite possible that such an interaction would have a dramatically different therapeutic consequence, one that could not have been arrived at using an in vitro assay.

The methods of the present invention simplify the evaluation, identification, and development of active agents for the treatment and prevention of conditions associated with serotonin-mediated cellular responses, such as depression, panic disorders, obsessive compulsive disorder, sleep disorders, eating disorders, nausea, vomiting, other gastrointestinal disorders, and migraines, and the side effects associated with these drugs. In general, the screening methods provide a facile means for selecting natural or synthesized product extracts or compounds of interest from a large population that are further evaluated and condensed to a few active and selective materials. Constituents of this pool are then purified and evaluated using the methods of the invention to determine their ability to modulate serotonin-mediated responses and conditions.

Test Extracts and Compounds

In general, novel drugs for the treatment or prevention of serotonin-mediated cellular responses and conditions are identified from large libraries of both natural products, synthetic (or semi-synthetic) extracts or chemical libraries, according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from, for example, Brandon Associates (Merrimack, N.H.) and Aldrich Chemical (Milwaukee, Wis.).

Alternatively, libraries of natural compounds in the form of bacterial, fungal, plant, and animal extracts are commercially available from a number of sources, including, but not limited to, Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art (e.g., by combinatorial chemistry methods or standard extraction and fractionation methods). Furthermore, if desired, any library or compound may be readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effects on compounds associated with serotonin-mediated cellular responses should be employed whenever possible.

When a crude extract is found to affect serotonin-mediated cellular responses or conditions, further fractionation of the positive lead extract is necessary to isolate chemical constituents responsible for the observed effect. Thus, the goal of the extraction, fractionation, and purification process is the careful characterization and identification of a chemical entity within the crude extract having activities that affect serotonin-mediated cellular responses. The same in vivo and in vitro assays described herein for the detection of activities in mixtures of compounds can be used to purify the active component and to test derivatives thereof. Methods of fractionation and purification of such heterogenous extracts are known in the art. If desired, compounds shown to be useful agents for the treatment of pathogenicity are chemically modified according to methods known in the art. Compounds identified as being of therapeutic value are subsequently analyzed using any standard animal model of serotonin-mediated cellular responses known in the art.

Assays to be used for identifying compounds that affect serotonin-mediated cellular responses include assaying locomotion rates of nematodes exposed to candidate compounds. It also includes adding a candidate compound to a cell and assaying serotonin reuptake transporter expression at the nucleic acid level or at the polypeptide level. The changes in serotonin reuptake transporter RNA levels can be monitored by Northern blots, or by highly sensitive quantitative RT-PCR assays. The changes in the levels of serotonin reuptake transporter polypeptides can be monitored through the use of standard Western blot analyses or immunohistochemistry.

Administration

A modulator of serotonin reuptake transporter biological activity may be administered within a pharmaceutically-acceptable diluent, carrier, or excipient, in unit dosage form. Conventional pharmaceutical practice may be employed to provide suitable formulations or compositions to administer the compounds to patients suffering from a condition associated with serotonin-mediated cellular responses. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, suppository, or oral. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences" ((18$^{th}$ edition), ed. A. Gennano, 1990, Mack Publishing Company, Easton, Pa.). Formulations for parenteral administration may contain, for example, excipients, sterile water, or saline, polyalkylene glycols, such as polyethylene glycol, oils of vegetable origin, or hydrogenated napthalenes. Biocompatible, biodegradable lactide polymers, lactide/glycolide copolymers, or polyoxyethylene-polyoxypropylene copolymers may be used to control the release of the compounds. Other potentially useful parenteral delivery systems for serotonin reuptake transporter modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with serotonin reuptake transporter mutant proteins, related genes, or other modulatory compounds may be combined with more traditional therapies for conditions associated with serotonin-mediated cellular responses. For example, a compound identified by the methods of the present invention may be combined with antidepressants, including a tricyclic antidepressant, monoamine oxidase inhibitor, or selective serotonin reuptake inhibitor, a migraine medication, or an anti-emetic.

The following examples are provided to illustrate the invention. These examples should not be construed as limiting.

EXAMPLES

Example 1

Identification of a Compound that Modulates the Biological Activity of a Nematode Serotonin Reuptake Transporter in a Liquid Locomotion Assay A nematode expressing either a wild-type or mutant *C. elegans* CeSERT gene, such as CeSERT(n823), CeSERT (n822), or CeSERT(n3314), is exposed to a test compound. The test compound is obtained from any number of sources, as described above, and each test compound is used in this assay at a variety of concentrations in order to determine the optimal dose that modulates the biological activity of a nematode serotonin reuptake transporter. Exposure of a nematode to a test compound is achieved by placing the desired test compound into a well of a 96-well polystyrene plate, followed by placing 20 nematodes into each well containing a test compound. After 5 to 20 minutes, the number of non-swimming nematodes is determined by viewing the worms under a dissecting microscope. This number is compared to the number of nematodes not swimming in a well to which the test compound vehicle, but no test compound, is added. If the number of non-swimming nematodes is greater in a well to which a test compound is added, then this test compound is identified as a compound that modulates the biological activity of a nematode serotonin reuptake transporter. However, one may also determine the number of swimming nematodes, relative to the total number of nematodes, in the presence and absence of the test compound and thereby identify a compound that modulates the biological activity of a nematode reuptake transporter.

In addition to swimming in a liquid locomotion assay, examples of defined behaviors that may be looked at to measure the biological activity of a serotonin reuptake transporter include alterations in locomotion, pharyngeal pumping, egg-laying, nose contraction, and defecation behaviors.

Example 2

Identification of a Compound that Modulates the Biological Activity of a Mammalian Serotonin Reuptake Transporter in a Liquid Locomotion Assay Transgenic nematodes in which the endogenous CeSERT gene is mutated and a mammalian CeSERT gene, for example, hSERT is expressed, is generated using standard techniques known to those skilled in the fields of nematode genetics and molecular biology. The nematodes are exposed to various concentrations of a test compound derived from any number of sources, as described above. Exposure of the nematodes to a test compound is achieved by placing the desired test compound into a well of a 96-well polystyrene plate, followed by placing 20 nematodes into each well containing a test compound. After 5 to 20 minutes, the number of nematodes not swimming is determined by viewing the nematodes under a microscope. This number is compared to the number of non-swimming transgenic nematodes expressing the same mammalian CeSERT gene in a well to which test compound vehicle, but no test compound, is added. If the number of non-swimming nematodes is greater in a well to which a test compound is added, then this test compound is identified as a compound that modulates the biological activity of a mammalian serotonin reuptake transporter. However, one may also determine the number of swimming nematodes, relative to the total number of nematodes, in the presence and absence of the test compound and thereby identify a compound that modulates the biological activity of a mammalian reuptake transporter.

Example 3

Determination as to Whether an Identified Compound Has a Secondary Target

Any compound identified to modulate the biological activity of a serotonin reuptake transporter using the assays described above may be further tested to determine if it also has a secondary target. To make this determination, a nematode expressing a mutated serotonin reuptake transporter is provided. This mutated serotonin reuptake transporter may be, for example, mutated CeSERT or hSERT and may have a reduced capacity to take up serotonin relative the wild-type protein.

Nematodes expressing a mutated serotonin reuptake transporter are exposed to the compound to be tested for a secondary target. Exposure of the nematodes to such a compound, is achieved by placing the compound into a well of a 96-well polystyrene plate, followed placing 20 nematodes into the same well. After 5 to 20 minutes, the biological activity of the nematodes exposed to the compound is measured and compared to the biological activity of nematodes that did not receive the compound. Examples of biological activities that may be measured include alterations in locomotion, pharyngeal pumping, egg-laying, nose contraction, and defecation behaviors. In order to determine the optimal concentration at which a biological activity is measured, each compound to be examined for a secondary target may be used in this assay at a variety of concentrations.

Example 4

The Use of CeSERT Deletion Mutants in the Identification of CeSERT Modulatory Compounds A truncated CeSERT polypeptide of the present invention that still maintains wild-type CeSERT activity may also be useful in identifying or designing SERT modulatory compounds. For example, we have determined that a wild-type CeSERT polypeptide that has been truncated to contain only the 421 most N-terminal amino acids (SEQ ID NO:9) still maintains wild-type polypeptide biological activity. This truncated CeSERT, or any other CeSERT polypeptide that has been further truncated, yet still maintains significant wild-type polypeptide biological activity, is used as a target for rational drug design. A therapeutic agent designed using the truncated CeSERT polypeptide may be more efficacious than a drug designed using the full-length polypeptide as a target, because the truncated polypeptide is a better-defined target. For example, a therapeutic agent that modulates the function of a truncated SERT might modulate the endogenous (full-length) SERT better than a drug that was originally selected to modulate the biological activity of a full-length SERT, and might also have fewer side effects.

Example 5
Use of High-throughput Screens to Identify Compounds that Modulate the Biological Activity of a SERT or Affect a Secondary Target of an Identified Compound In vivo assays for the identification of compounds that modulate the biological activity of a SERT or affect a secondary target of an identified compound can be accelerated. The rate-limiting step in the identification of modulatory compounds and secondary targets is placing the nematodes into wells containing test compounds. This process can be made more efficient using, for example, a Large Particle Dispenser (Becton, Dickinson and Co., Franklin Lakes, N.J.). Using this dispenser, the desired number of nematodes (for example, 20) can be sorted into each well of a 96- or 384-well plate containing the compound to be tested or control. Preferably the nematodes have a mutated SERT gene and express the wild-type human SERT gene.

After 5 to 20 minutes, the number of non-swimming nematodes is determined by viewing the worms under a dissecting microscope. This visual inspection can be quickly assessed as one is simply determining whether or not there is locomotion in each well. If a well contains nematodes that are no longer moving, then the test compound in that specific well is identified as a compound that modulates the biological activity of a nematode serotonin reuptake transporter. Automated high-throughput ways to speed up the process of determining if the animals are moving also exist and can be incorporated into the screen.

Any compound identified to modulate the biological activity of a serotonin reuptake transporter using the assays described above may be further tested to determine if it also has a secondary target. To make this determination, a nematode expressing a mutated serotonin reuptake transporter is provided. This mutated serotonin reuptake transporter may be, for example, mutated CeSERT or hSERT.

Nematodes expressing a mutated serotonin reuptake transporter are sorted into wells containing the compounds of interest or controls using a Large Particle Dispenser. After 5 to 20 minutes, the biological activity of the nematodes exposed to the compound is measured and compared to the biological activity of nematodes that did not receive the compound. Examples of biological activities that may be measured include alterations in locomotion, pharyngeal pumping, egg-laying, and defecation behaviors. If nematodes carrying a mutated CeSERT or hSERT are affected by a test compound, this compound is then identified as having SERT-independent effects (side effects) resulting from secondary targets of the test compound.

Example 6
Materials and Methods
mod-5 Mapping, Cloning, and cDNA Isolation

Nematodes were grown at 20° C. using *E. coli* strain HB101 as the food source (Sawin et al., *Neuron* 26:619–623, 2000). Wild-type animals were *C. elegans* strain N2. mod-5(n822) and mod-5(n823) were isolated from a genetic screen in which clonal populations of F3 animals descended from $P_0$ animals mutagenized with ethyl methanesulphonate (Brenner, *Science* 282:2012–2018, 1974) were pretreated with serotonin (15 min incubation in 500 µl of 13 mM serotonin followed by two washes with M9) and then examined for the presence of the NSMs using FIF (Sulston et al., *J Comp Neurol* 163:215–226, 1975). mod-5(n3314) was isolated from a library of animals mutagenized with UV/trimethylpsoralen (Jansen et al., *Nat Genet* 17:119–121, 1997). The deletion library was constructed essentially as described in Jansen et al. (*Nat Genet* 17:119–121, 1997) and Liu et al. (*Genome Res* 9:859–867, 1999). mod-5(n3314) was backcrossed to the wild-type six times prior to behavioral assays. Furthermore, mod-5(n823) was mapped to LG I based upon two-factor linkage to dpy-5 unc-75 I. The following three-factor data were obtained: mod-5 (47/47) dpy-5 (0/47) unc-75, mod-5 (35/35) unc-73 (0/35) lin-44 dpy-5, lin-6 (27/27) lin-17 (0/27) mod-5, lin-17 (0/13) mod-5, and fog-1 (3/26) mod-5 (23/26) unc-11. All mapping experiments were performed by mating hermaphrodites homozygous for the recombinant chromosome with mod-5 (n823) males and scoring the F1 cross progeny for serotonin hypersensitivity at 5 min in 10 mM serotonin.

Long-range PCR was performed using the Advantage cDNA PCR kit (Clontech). DNA sequences were determined using an automated ABI 373A DNA sequencer (Applied Biosystems). RT-PCR was performed with primers corresponding to exons predicted by Genefinder (The *C. elegans* Sequencing Consortium, 1998). The 5' and 3' ends of the mod-5 cDNA were determined using 5'- and 3'-RACE kits (Gibco), respectively. We showed that the cDNA is functional (see above), which indicates that no exons are missing in the predicted gene structure. The mod-5 open reading frame is 2,016 bp within a 2,594 bp cDNA. The extent of the 1,688 bp n3314 deletion is depicted.

To construct the mod-5 minigene, we used PCR and primers that contained restriction enzyme sites at their ends to amplify 2.7 kb of the mod-5 promoter region. A Pst I-Bam HI fragment of this PCR product was ligated into the pPD49.26 vector digested with Pst I and Bam HI. This mod-5 promoter construct was then digested with Nco I and Sac I and ligated to an Nco I-Sac I fragment of the mod-5 coding region, PCR-amplified in a manner similar to that used for the mod-5 promoter region.

*C. elegans* Germline Transformation

Germline transformation experiments (Mello et al., *EMBO J* 10:3959–3970, 1991) were performed by injecting various constructs with 80 µg/ml pL15EK (which contains the wild-type lin-15 gene) into a mod-5(n823); lin-15 (n765ts) strain and scoring serotonin sensitivity in transgenic lines that produced non-Lin progeny at 22.5° C.

Liquid Locomotion Assay

Fluoxetine (HCl salt, Sigma) was dissolved in water, and 400 µl of a 25× stock solution were added to each 5 cm plate, containing approximately 10 ml of agar, to obtain the various final concentrations of fluoxetine. The plates were allowed to dry at room temperature with their lids removed for more than 2 hours.

Animals to be tested for sensitivity or insensitivity to serotonin in this liquid locomotion assay were picked as L4 animals 16–20 hours prior to assay and the plates were coded so that the experimenter was blind to the genotype of the animals to be scored. On the day of the assay, serotonin (as a creatinine sulphate salt) was dissolved just before use, in M9, at the required concentrations, and 200 µl were aliquoted to the wells of a flat-bottomed 96-well polystyrene plate. To assay serotonin hypersensitivity, we placed 20 animals in 200 μl of serotonin solution (creatinine sulphate salt, Sigma, dissolved in M9 buffer; Wood et al., 1988) in 96-well microtiter wells and scored the swimming behavior of the animals as either active or immobile at 5 min; an animal was scored as immobile if it did not exhibit any swimming motion for a period of 5 seconds. Fluoxetine-induced paralysis was scored in a similar manner at 10 min.

For the experiment shown in FIG. 2, well-fed and food-deprived animals were transferred to assay plates with or without a bacterial lawn, and the locomotory rate of each animal was recorded after 5 min; food-deprived animals were transferred to plates without bacteria 30 min prior to the transfer to locomotory assay plates as is also described in Sawin et al. (*Neuron* 26:619–623, 2000). At least 10 trials were performed for each genotype for each condition. For FIG. 2, each trial involved testing at least five animals for each of the conditions; a given animal was tested in only one condition. p values were calculated by comparing the combined data for the mutants from all of the separate trials under one set of conditions to the combined data for the wild-type animals assayed in parallel under the same conditions. In FIG. 2B the data were obtained from three well-fed animals of each ablation state, seven mock-ablated and food-deprived animals, and 12 NSM-ablated and food-deprived animals. In FIG. 2D, serotonin dose-response curves for wild-type and mod-5 mutant animals were generated from averages of five trials with 20 animals of each genotype at each concentration in which animals were scored for movement after 5 min.

Additional Locomotion Assays

Alternatively, nematodes to be tested in a non-liquid locomotion assay were picked as L4 animals 16–20 hours prior to the assay. Locomotion was assayed by placing the nematode on an assay plate (prepared by spreading a solution of E. coli strain HB101 in NGM agar in 5 cm plates, using a ring with an inner diameter of approximately 1 cm and an outer diameter of approximately 3.5 cm, and allowing the bacteria to grow 13–15 hours at 37 C), observing each nematode under a dissecting microscope for 20 seconds, and counting the number of dorsal-ventral bends that occurred in the anterior portion of the body during the interval.

For satiated animals, locomotion rates were assayed by removing 5 animals from plates with ample bacteria, washing them in S-basal buffer, and transferring them to the clear zone of the bacterial lawn of an assay plate using a capillary pipette. Beginning 5 minutes after transfer, the number of body bends was counted as described above. This procedure was performed for each of the 5 animals.

To assay locomotion rates in food-deprived animals, 5–15 animals were removed from plates with ample food, washed twice in S-basal buffer, and transferred to 5 cm NGM agar plates without bacteria. Food-deprived animals were incubated on these plates for 30 minutes at room temperature, and then were transferred to assay plates. Locomotion rates were assayed as described above for satiated animals.

As compared to wild-type nematodes, the n822 and n823 mutants obtained from a screen for *C. elegans* defective in staining of the serotonergic NSM neurons, exhibit a recessive phenotype of slowing down more after being deprived of bacteria and then returned to a bacterial lawn in the locomotion assays. This same effect was observed in the n3314 mutants.

Laser Microsurgery

Neurons were ablated during the second larval stage using a laser microbeam, as described in Avery and Horvitz, (*Cell* 51:1071–1078, 1987) and Bargmann and Horvitz, (*Neuron* 7:729–742, 1991). Behavioral assays of young adult animals were performed two days later. Mock-ablated animals were animals transferred to agar pads and anesthetized in parallel to the animals that underwent laser ablation. Sawin et al. (*Neuron* 26:619–623, 2000) describe details concerning how ablated animals were assayed sequentially in each of the different behavioral conditions.

Egg-laying Assays

Egg-laying assays were performed as described in Trent et al. (*Genetics* 104:619–647, 1983). Briefly, one day-old adult animals (staged by picking late L4 animals 36 hours prior to the assay) were placed in wells of microtiter dishes containing 100 μl of 12.5 mM serotonin or 500 μg/ml fluoxetine, and the number of eggs laid was counted after 90 minutes.

Serotonin-uptake Assays in vivo

FIF assays were performed as described by Sulston et al. (*J Comp Neurol* 163:215–226, 1975). For the anti-serotonin antisera experiments shown in FIG. 1B, mod-5(n823); cat-4 and cat-4; lin-15(n765ts) double mutants were grown at 20° C., and animals of both genotypes were incubated separately on plates containing 2 mM serotonin and bacteria (see Sawin et al. (*Neuron* 26:619–623, 2000) for details concerning how plates were prepared) for two hours and then incubated on plates with bacteria but without serotonin for 30 min. Controls without exogenous serotonin were similarly treated in parallel. Prior to fixation, mod-5(n823); cat-4 and cat-4; lin-15 double mutants preincubated on serotonin-containing plates were combined, and mod-5(n823); cat-4 and cat-4; lin-15 double mutants preincubated on control plates were combined. Serotonin staining was performed as described by Desai et al. (*Nature* 336:638–646, 1988) using affinity-purified rabbit polyclonal anti-serotonin antisera. The cat-4; lin-15 mutants were not defective in the uptake of serotonin and served as internal controls for each staining reaction. These animals could be distinguished from the test animals by the Multivulva phenotype caused by lin-15. Neurons with bright staining in cell bodies, axonal processes, and varicosities were termed "bright" and neurons with weak staining in just the cell bodies and axonal processes were termed "weak." For the results in Table 1, the procedure was essentially the same, except that the animals experienced an additional 1 hour incubation on control or fluoxetine-containing plates prior to the 2 hour incubation with serotonin but did not experience the 30 min incubation on plates without drug after the serotonin preincubation (see Table 1 legend for details). lin-15 adult animals, grown at 22.5° C. were added to all plates at the first incubation step and these animals served as internal controls for the staining reaction.

MOD-5-mediated Uptake in Mammalian Cells

We used a modified version of the MSCVpac vector (Hawley et al., *Gene Ther* 1:136–138, 1994) in which the pac gene had been replaced with the gfp gene (GFP vector). We modified the GFP vector as follows: The ends of a Bgl II-Mfe I fragment containing the entire mod-5 cDNA were blunted using the Klenow fragment of DNA polymerase I and then ligated to the GFP vector digested with Hpa I, placing mod-5 under the control of the retroviral long terminal repeat promoter (GFPMOD-5). The Phoenix packaging cell line (ATCC #CRL-1817) was used to generate virus containing either GFPMOD-5 or GFP vector. HEK293 cells were infected with these viral stocks in the presence of 4 mg/ml polybrene, and clones expressing high levels of GFP were isolated using a fluorescence activated cell sorter (FACstar or FACSvantage; Becton Dickinson). The GFPMOD-5 clones were then screened for MOD-5 CeSERT-mediated [$^3$H]serotonin uptake activity, and one clone was chosen for use in all further uptake experiments. Cells were plated at $10^6$ cells/well of a 6-well dish and allowed to grow overnight before being assayed. Cells were incubated in prewarmed wash buffer (120 mM NaCl, 10 mM HEPES pH 7.4, 4.7 mM KCl, 2.2 mM $CaCl_2$, 1.2 mM $KH_2PO_4$, 1.2 mM $MgSO_4$, 1.8 mg/ml glucose, 100 µM pargyline, 100 µM ascorbic acid) for 10 min at 37° C. and the buffer was then replaced with prewarmed wash buffer plus substrate.

Figure 4B:
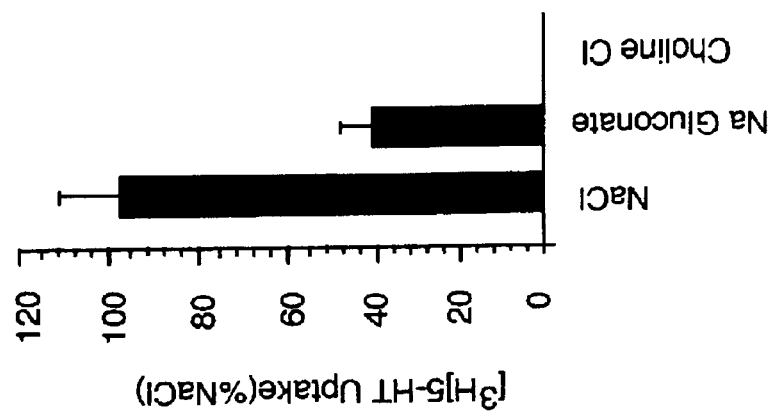
FIG. 4 shows the physiological characterization of MOD-5 CeSERT. Panel A shows the time dependence of MOD-5 CeSERT-mediated [$^3$H]serotonin transport. GFPMOD-5 (circles) and the GFP vector (squares) are shown. Panel B shows the dependence of MOD-5 CeSERT-mediated [$^3$H]serotonin transport on $Na^+$ and $Cl^-$ ions in the external buffer. Panel C shows MOD-5 CeSERT-mediated [$^3$H]serotonin transport as a function of serotonin concentration. The insert is an Eadie-Hoftsee transformation (Stryer, *Biochemistry*, 4th Edition. New York: W. H. Freeman, 1995) of the data where $K_m$=150±8 nM; $V_{max}$= 8.31×10$^{-9}$ nmoles per cell per min. Panel D shows that MOD-5 CeSERT-mediated transport was specific for [$^3$H] serotonin. Panel E shows antagonism of MOD-5 CeSERT-mediated serotonin uptake by showing inhibition curves for SSRIs and other transporter inhibitors. The extent of [$^3$H] serotonin uptake is plotted as the percentage of [$^3$H] serotonin uptake observed in the absence of antagonists vs. log [inhibitor]. Error bars indicate the standard error of the mean.
Figure 4A:
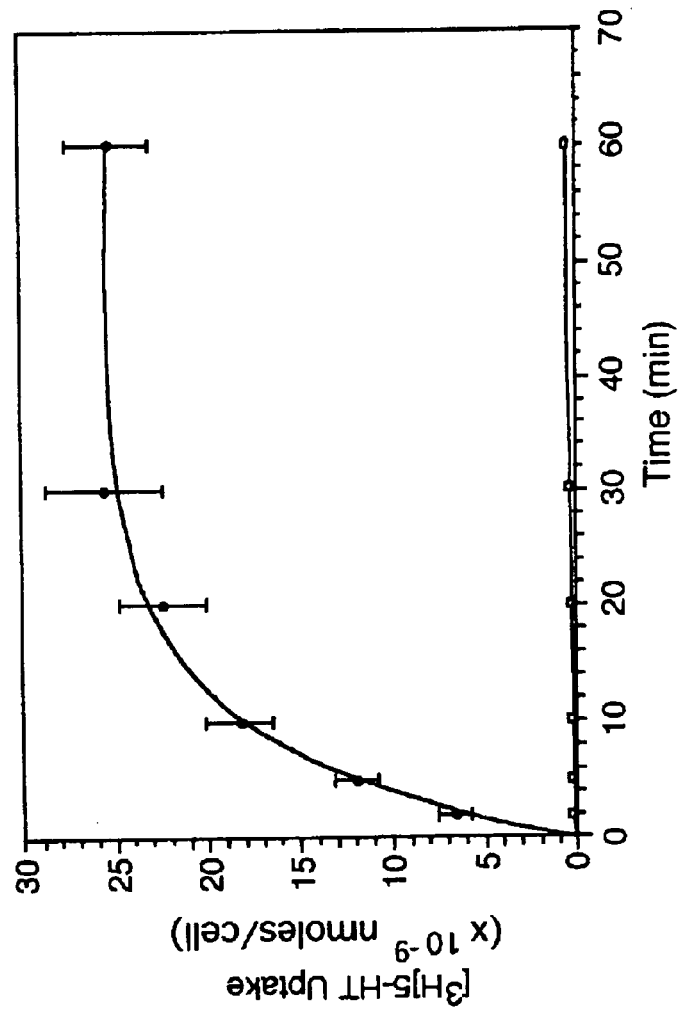
Figure 4C:
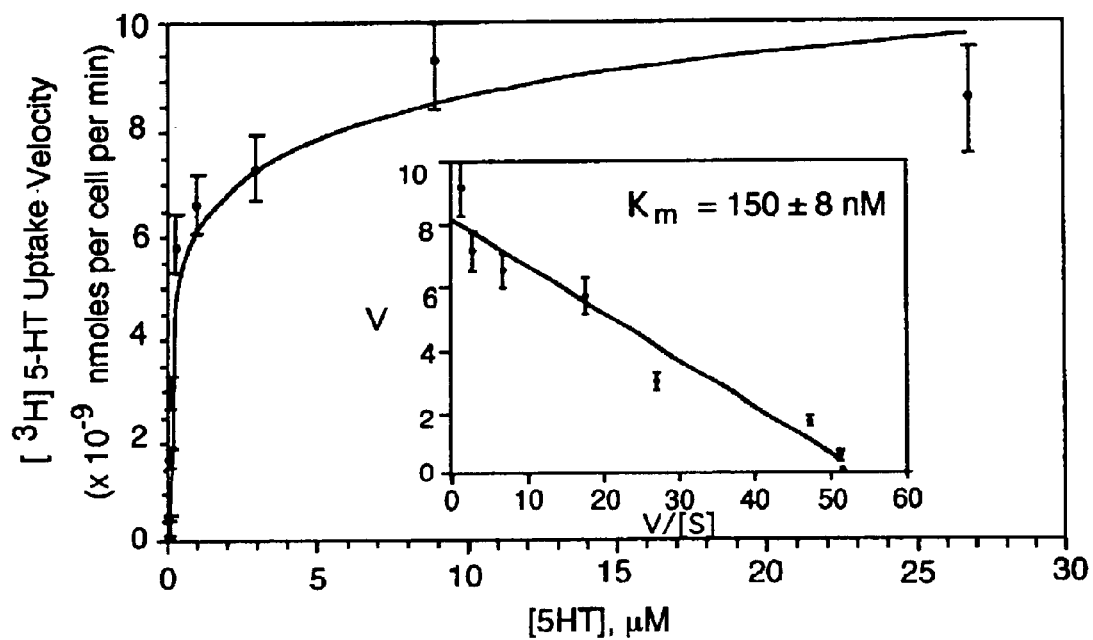
Figure 4D:
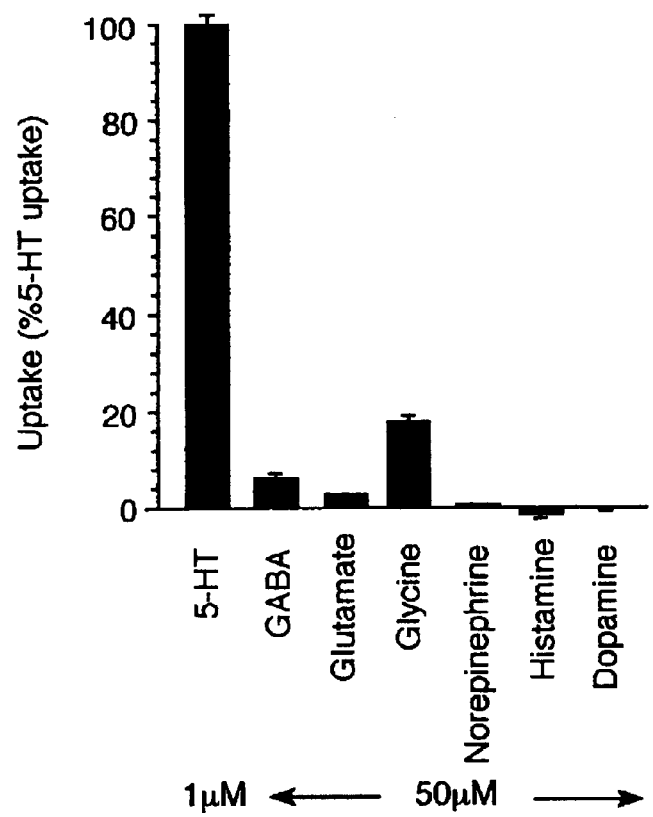
Figure 4E:
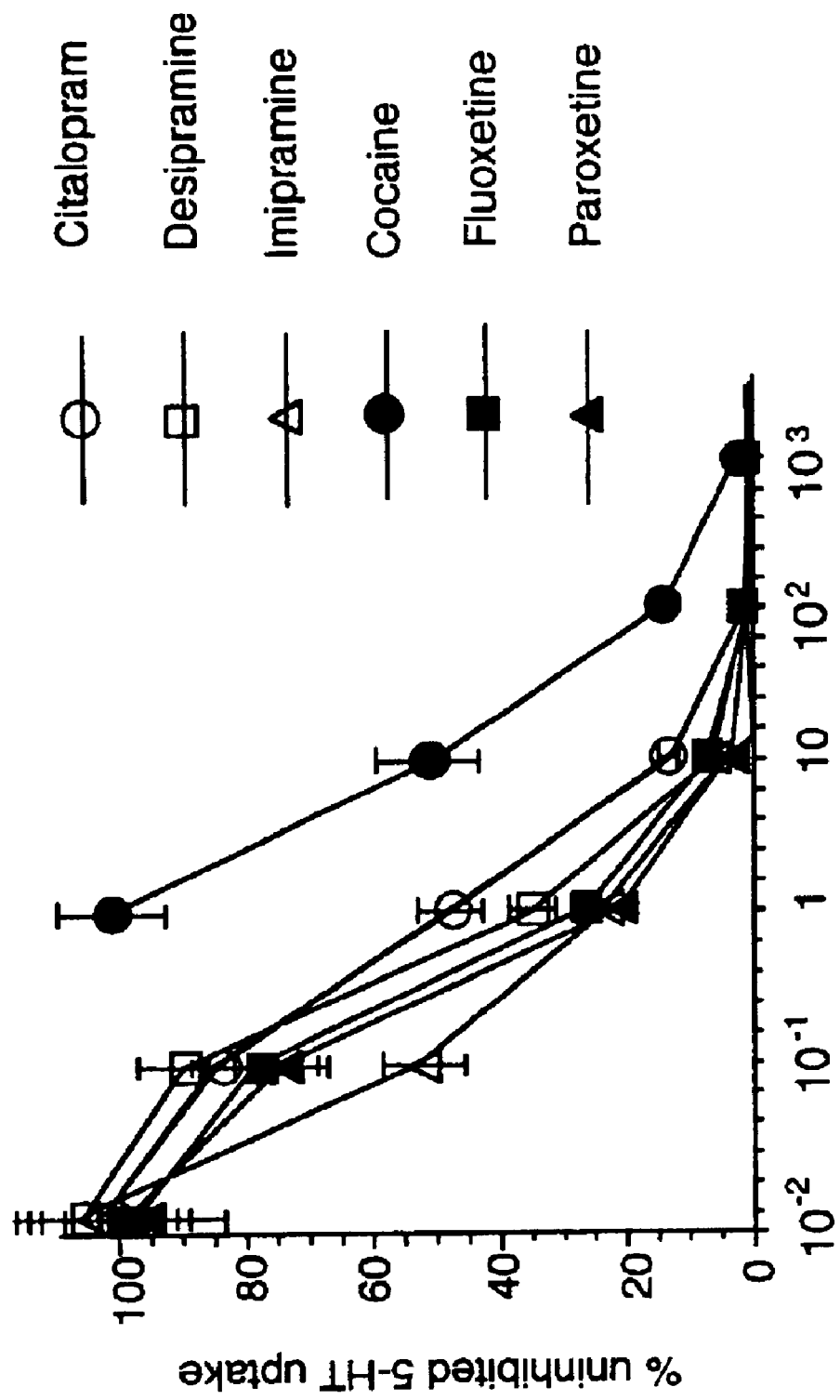

In FIG. 4B, the NaCl was substituted with an equivalent amount of sodium gluconate or choline chloride. Except for the trials shown in FIGS. 4C and D, 50 nM [$^3$H]serotonin was used as substrate (there was no dilution with non-radioactive substrate in these experiments). Since micromolar amounts of substrate were used in the trials shown in FIGS. 4C and D, radiolabeled substrates were diluted with non-radioactive substrate to maintain a specific activity of 0.1 Ci/mmol. In FIG. 4D, assays were performed with 1 µM [$^3$H]serotonin and 50 µM of each of the other radiolabeled neurotransmitters, and the results are presented as a percentage of normalized 1 µM [$^3$H]serotonin uptake. There was no detectable transport when neurotransmitters other than serotonin were added at 1 µM. Uptake was allowed to proceed at 37° C. for varying times for the time course and for 10 min in all other experiments. Cells were then washed three times with ice-cold wash buffer, solubilized in 1% SDS and the radioactivity retained in the cells was determined by liquid scintillation. Cell numbers, quantified in parallel wells taken through all steps of the assay, were used to convert counts per minute (cpm) to nmoles per cell per min. The specific uptake of each substrate for each condition was obtained by subtracting the average value obtained from at least three trials with the GFP vector cell line from the average value obtained from at least six trials with the GFPMOD-5 cell line. Inhibitor $K_i$ values were determined from concentration vs. uptake profiles after adjustment for substrate concentrations (Cheng and Prusoff, *Biochem Pharmacol* 22:3099–3108, 1973). Statistical significance was evaluated using the Student's t-test (Statview).

Other Preferred Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications mentioned in this specification are herein incorporated by reference to the same extent as if each independent publication or patent application was specifically and individually indicated to be incorporated by reference.

What is claimed is:

1. A method for determining whether a test compound, which modulates the uptake of serotonin by a serotonin reuptake transporter (SERT), has an effect on a secondary target, said method comprising the steps of:
   (a) contacting a *Caenorhabditis elegans* nematode lacking a wild-type SERT polypeptide and expressing a mutated *Caenorhabditis elegans* SERT (CeSERT) polypeptide selected from the group consisting of a CeSERT(n822) polypeptide, a CeSERT(n823) polypeptide, and a CeSERT(n3314) polypeptide with said compound, wherein said mutated CeSERT polypeptide has a reduced capacity to take up serotonin relative to wild-type; and
   (b) analyzing said nematode for an effect of said contacting on a defined behavior by said nematode, wherein a difference in said defined behavior by said nematode, relative to said defined behavior by a *Caenorhabditis elegans* nematode expressing a mutated CeSERT polypeptide but not contacted with said compound, indicates said compound has an effect on a secondary target.

2. The method of claim 1, wherein steps (a) and (b) are repeated using a *Caenorhabditis elegans* nematode selected from at least two *Caenorhabditis elegans* nematodes expressing a mutated CeSERT polypeptide selected from the group consisting of a CeSERT(n822) polypeptide, a CeSERT(n823) polypeptide, and a CeSERT(n3314) polypeptide, wherein said mutated CeSERT polypeptide differs from said mutated CeSERT polypeptide of step (a).

3. The method of claim 1, wherein said mutated CeSERT polypeptide is a complete loss-of-function.

4. The method of claim 1, wherein said method comprises a liquid locomotion assay.

5. The method of claim 1, wherein said defined behavior is movement, pharyngeal pumping, egg-laying, nose contraction, or defecation.

6. The method of claim 1, wherein said compound is from a class of compounds selected from the group consisting of antidepressants, migraine medications, and anti-emetics.

7. The method of claim 6, wherein said antidepressant is a selective serotonin reuptake inhibitor.

8. The method of claim 6, wherein said antidepressant is a tricyclic antidepressant.

9. The method of claim 6, wherein said antidepressant is a monoamine oxidase inhibitor.

10. The method of claim 1, wherein said test compound is administered at more than one concentration.

* * * * *

UNITED STATES PATENT AND TRADEMARK OFFICE
CERTIFICATE OF CORRECTION

PATENT NO.       : 6,841,145 B2
APPLICATION NO.  : 09/843598
DATED            : January 11, 2005
INVENTOR(S)      : Horvitz et al.

It is certified that error appears in the above-identified patent and that said Letters Patent is hereby corrected as shown below:

Column 1, lines 14-20: Replace "This research was funded, in part, by NIH Grant RM37GM024663. The U.S. Government has certain rights to the invention" with --This invention was made with government support under grant number R37 GM024663 awarded by the NIH. The government has certain rights in this invention.--

Signed and Sealed this
Fourteenth Day of June, 2011

David J. Kappos
*Director of the United States Patent and Trademark Office*

SEQUENCE LISTING

<160> NUMBER OF SEQ ID NOS: 11

<210> SEQ ID NO 1
<211> LENGTH: 2016
<212> TYPE: DNA
<213> ORGANISM: Caenorhabditis elegans

<400> SEQUENCE: 1

| | | | | | | |
|---|---|---|---|---|---|---|
| atgctgcgtt | ggcattccgt | ccggaggaaa | cagcaccagc | agctgcaagc | tgaactctcc | 60 |
| agcggtgcag | ctagcatgct | gtccgcgcca | gaatctcggc | gtgtcagccg | atcgatgagt | 120 |
| gttaaagcac | cgacagcatc | agaatacatg | ccattatcag | ttgccgataa | gccctaaca | 180 |
| ctaaccgtat | caacttcaca | cagtattgat | ccaaatgagc | caatcgctgc | tctcggtggt | 240 |
| ctcacaccga | caaaagaagg | ccgagttgcc | gcactgcgaa | gacggagttc | aatggttcgt | 300 |
| gataaatggg | caactaaaat | ggaattcctg | ttggccgtcg | ttggatatgc | agttgatttg | 360 |
| ggtaatatat | ggcgattccc | atcagtatgc | tacaaacacg | gtggcggtgc | ttttcttatt | 420 |
| ccatatttca | ttatgttaat | gatcggagga | cttcccatgt | tctatatgga | acttgtactc | 480 |
| ggacaatttc | atcggtcagg | atgtgttagt | atatggagaa | aggtgtgccc | gttgtttcga | 540 |
| ggaatcggtt | acggtatctg | ctgtatttgc | acgttcatag | ccattttcta | taatgcgatc | 600 |
| atcgctcaag | ccgtctattt | tgctattgtt | tcactttcaa | aaatttggga | ttccgaagtt | 660 |
| ccgtgggcgt | catgtggcaa | tccgtggaat | acaccgagat | gctcagatga | cctcaacgtg | 720 |
| acaatatcta | gaaatgggac | accattgacc | actccgtcag | aggaatatta | tttatacaaa | 780 |
| gtccttgaag | ttcaaaaatc | aacaggattc | gatgatcttg | gaggtgtaaa | aacttcaatg | 840 |
| gcagtgtgcc | tactcgctgt | atttataatg | gtttactttg | ctctttggaa | gggtccacag | 900 |
| tcgtctggaa | aaattgtttg | ggtgactgca | acagctccat | atattattct | aagtattctt | 960 |

```
cttatacgtg gacttcttct tcctggagca agaatggtc tctattatta tgtgacaccg    1020
gatttcgaga aactcaagga tcctgcagta tggtcggctg ctgctacaca gatttcttc    1080 tcacttggac caggattcgg ggtgctgctc gcgctgagca gttacaatga ttttaacaat    1140
aactgctatc gtgacgccgt cactatctcc atcattaact gtgccacgtc attctttcc    1200 ggatgtgttg tattctctac acttggctat atgtctcttc tcaccaataa accgattaat    1260
gaggtagttg gagaacacga cgcctctcta atcttcatcg tctaccccca gccctcgca    1320 acaatggatt acagttgttt ctggtctttc atcttttcg tcatgctaat cactcttgga    1380
atcgactcca cttttgctgg aatcgaagca tttatacgg gattctgtga tgagtcgagg    1440
tttttgtcga aaaatcgaaa atggttcgt ctggtcattt gcatcattta ttacttcctc    1500
agctttcccg ctatcagcta tggtggtcaa ttcgtgatcc cgttcctgga tgaatatgga    1560
gtttctctat cagttctgtt cattgtcacc tgcgaaatga ttgcagtctg ctggttttac    1620
ggtgttgatc agttctcaaa agatattcgt gctatgctgg gattctatcc tggaatttat    1680
tggagagtct gctggacgtg ttctccggtt tttataagtg tgatattcat tatgactgtc    1740
tacaatagtt cgttcaagcc aattcaaatg gctagctaca ctttccctg gtggagtgtt    1800 attttgggtt ggtcctgag acttctctca gtcctcgcaa ttcctgtctt cgcaataatc    1860
tacctgctca gcggtaccgg cacactttac gaacgcttcc gatgggcaat aactcctcaa    1920
caacgccgaa attcggcgac ttctctcgcc gctgatccca cacaaattat cgatagttct    1980
cttttagatc caattcatac acttactcca gtttag                              2016

<210> SEQ ID NO 2
<211> LENGTH: 2016
<212> TYPE: DNA
<213> ORGANISM: Caenorhabditis elegans

<400> SEQUENCE: 2
atgctgcgtt ggcattccgt ccggaggaaa cagcaccagc agctgcaagc tgaactctcc     60
agcggtgcag ctagcatgct gtccgcgcca gaatctcggc gtgtcagccg atcgatgagt    120
gttaaagcac cgacagcatc agaatacatg ccattatcag ttgccgataa gcccctaaca    180
ctaaccgtat caacttcaca cagtattgat ccaaatgagc caatcgctgc tctcggtggt    240
ctcacaccga caaaagaagg ccgagttgcc gcactgcgaa gacggagttc aatggttcgt    300
gataaatggg caactaaaat ggaattcctg ttggccgtcg ttggatatgc agttgatttg    360
ggtaatatat ggcgattccc atcagtatgc tacaaacacg gtggcggtgc ttttcttatt    420
ccatatttca ttatgttaat gatcggagga cttcccatgt tctatatgga acttgtactc    480
ggacaatttc atcggtcagg atgtgttagt atatggagaa aggtgtgccc gttgttttcga   540 ggaatcggtt acggtatctg ctgtatttgc acgttcatag ccattttcta taatgcgatc    600
atcgctcaag ccgtctattt tgctattgtt tcactttcaa aaatttggga ttccgaagtt    660
ccgtgggcgt catgaggcaa tccgtggaat acaccgagat gctcagatga cctcaacgtg    720
acaatatcta gaaatgggac accattgacc actccgtcag aggaatatta tttatacaaa    780
gtccttgaag ttcaaaaatc aacaggattc gatgatcttg gaggtgtaaa aacttcaatg    840
gcagtgtgcc tactcgctgt atttataatg gtttacttg ctctttggaa gggtccacag    900
tcgtctggaa aaattgtttg ggtgactgca acagctccat atattattct aagtattctt    960
cttatacgtg gacttcttct tcctggagca agaatggtc tctattatta tgtgacaccg    1020
```

```
gatttcgaga aactcaagga tcctgcagta tggtcggctg ctgctacaca gatttttcttc   1080 tcacttggac caggattcgg ggtgctgctc gcgctgagca gttacaatga tttttaacaat   1140 aactgctatc gtgacgccgt cactatctcc atcattaact gtgccacgtc attcttttcc   1200
ggatgtgttg tattctctac acttggctat atgtctcttc tcaccaataa accgattaat   1260
gaggtagttg gagaacacga cgcctctcta atcttcatcg tctacccca agccctcgca   1320 acaatggatt acagttgttt ctggtctttc atcttttcg tcatgctaat cactcttgga   1380
atcgactcca ctttgctgg aatcgaagca tttatcacgg gattctgtga tgagtcgagg   1440 ttttttgtcga aaaatcgaaa atggttcgtg ctggtcattt gcatcattta ttacttcctc   1500
agctttcccg ctatcagcta tggtggtcaa ttcgtgatcc cgttcctgga tgaatatgga   1560
gtttctctat cagttctgtt cattgtcacc tgcgaaatga ttgcagtctg ctggttttac   1620
ggtgttgatc agttctcaaa agatattcgt gctatgctgg gattctatcc tggaattat   1680 tggagagtct gctggacgtg ttctccggtt tttataagtg tgatattcat tatgactgtc   1740
tacaatagtt cgttcaagcc aattcaaatg gctagctaca cttttcccctg gtggagtgtt   1800 attttgggtt ggttcctgag acttctctca gtcctcgcaa ttcctgtctt cgcaataatc   1860
tacctgctca gcggtaccgg cacactttac gaacgcttcc gatgggcaat aactcctcaa   1920
caacgccgaa attcggcgac ttctctcgcc gctgatccca cacaaattat cgatagttct   1980 ctttagatc caattcatac acttactcca gtttag                              2016

<210> SEQ ID NO 3
<211> LENGTH: 2016
<212> TYPE: DNA
<213> ORGANISM: Caenorhabditis elegans

<400> SEQUENCE: 3
atgctgcgtt ggcattccgt ccggaggaaa cagcaccagc agctgcaagc tgaactctcc     60
agcggtgcag ctagcatgct gtccgcgcca gaatctcggc gtgtcagccg atcgatgagt    120
gttaaagcac cgacagcatc agaatacatg ccattatcag ttgccgataa gcccctaaca    180
ctaaccgtat caacttcaca cagtattgat ccaaatgagc caatcgctgc tctcggtggt    240
ctcacaccga caaagaaagg ccgagttgcc gcactgcgaa gacggagttc aatggttcgt    300
gataaatggg caactaaaat ggaattcctg ttggccgtcg ttggatatgc agttgatttg    360
ggtaatatat ggcgattccc atcagtatgc tacaaacacg tggcggtgc ttttcttatt    420 ccatatttca ttatgttaat gatcggagga cttcccatgt tctatatgga acttgtactc    480
ggacaatttc atcggtcagg atgtgttagt atatggagaa aggtgtgccc gttgtttcga    540
ggaatcggtt acggtatctg ctgtatttgc acgttcatag ccattttcta taatgcgatc    600
atcgctcaag ccgtctattt tgctattgtt tcactttcaa aaatttggga ttccgaagtt    660
ccgtgggcgt catgtggcaa tccgtggaat acaccgagat gctcagatga cctcaacgtg    720
acaatatcta gaaatgggac accattgacc actccgtcag aggaatatta tttatacaaa    780
gtccttgaag ttcaaaaatc aacaggattc gatgatcttg gaggtgtaaa aacttcaatg    840
gcagtgtgcc tactcgctgt atttataatg gtttactttg ctcttggaa gggtccacag    900 tcgtctggaa aaattgtttg ggtgactgca acagctccat atattattct aagtattctt    960
cttatacgtg gacttcttct tcctggagca agaatggtc tctattatta tgtgacaccg    1020
gatttcgaga aactcaagga tcctgcagta tggtcggctg ctgctacaca gatttttcttc   1080 tcacttggac caggattcgg ggtgctgctc gcgctgagca gttacaatga tttttaacaat   1140
```

-continued

```
aactgctatc gtgacgccgt cactatctcc atcattaact gtgccacgtc attcttttcc    1200
ggatgtgttg tattctctac acttggctat atgtctcttc tcaccaataa accgattaat    1260
gaggtagttg gagaacacga cgcctctcta atcttcatcg tctaccccca agccctcgca    1320
acaatggatt acagttgttt ctggtctttc atcttttcg tcatgctaat cactcttgga    1380
atcgactcca cttttgctgg aatcgaagca tttatcacgg gattctgtga tgagtcgagg    1440
tttttgtcga aaaatcgaaa atggttcgtg ctggtcattt gcatcattta ttacttcctc    1500
agctttcccg ctatcagcta tggtggtcaa ttcgtgatcc cgttcctgga tgaatatgga    1560
gtttctctat cagttctgtt cattgtcacc tgcgaaatga ttgcagtctg ctggttttac    1620
ggtgttgatc agttctcaaa agatattcgt gctatgctgg gattctatcc tggaatttat    1680
tggagagtct gctggacgtg ttcttcggtt tttataagtg tgatattcat tatgactgtc    1740
tacaatagtt cgttcaagcc aattcaaatg gctagctaca cttttcccctg gtggagtgtt    1800
attttgggtt ggttcctgag acttctctca gtcctcgcaa ttcctgtctt cgcaataatc    1860
tacctgctca gcggtaccgg cacactttac gaacgcttcc gatgggcaat aactcctcaa    1920
caacgccgaa attcggcgac ttctctcgcc gctgatccca cacaaattat cgatagttct    1980
cttttagatc caattcatac acttactcca gtttag                              2016
```

<210> SEQ ID NO 4
<211> LENGTH: 1370
<212> TYPE: DNA
<213> ORGANISM: Caenorhabditis elegans

<400> SEQUENCE: 4

```
atgctgcgtt ggcattccgt ccggaggaaa cagcaccagc agctgcaagc tgaactctcc      60
agcggtgcag ctagcatgct gtccgcgcca gaatctcggc gtgtcagccg atcgatgagt     120
gttaaagata caaagtcctt gaagttcaaa atcaacagg attcgatgat cttggaggtg     180
taaaaacttc aatggcagtg tgcctactcg ctgtatttat aatggtttac tttgctctttt    240
ggaagggtcc acagtcgtct ggaaaaattg tttgggtgac tgcaacagct ccatatatta    300
ttctaagtat tcttcttata cgtggacttc ttcttcctgg agcaaagaat ggtctctatt    360
attatgtgac accggatttc gagaaactca aggatcctgc agtatggtcg ctgctgcta    420
cacagatttt cttctcactt ggaccaggat tcggggtgct gctcgcgctg agcagttaca    480
atgattttaa caataactgc tatcgtgacg ccgtcactat ctccatcatt aactgtgcca    540
cgtcattctt ttccggatgt gttgtattct ctacacttgg ctatatgtct cttctcacca    600
ataaaccgat taatgaggta gttggagaac acgacgcctc tctaatcttc atcgtctacc    660
cccaagccct cgcaacaatg gattacagtt gtttctggtc tttcatcttt tcgtcatgc    720
taatcactct tggaatcgac tccacttttg ctggaatcga agcatttatc acggattct    780
gtgatgagtc gaggttttg tcgaaaaatc gaaaatggtt cgtgctggtc atttgcatca    840
tttattactt cctcagcttt cccgctatca gctatggtgg tcaattcgtg atcccgttcc    900
tggatgaata tggagtttct ctatcagttc tgttcattgt cacctgcgaa atgattgcag    960
tctgctggtt ttacggtgtt gatcagttct caaaagatat tcgtgctatg ctgggattct   1020
atcctggaat ttattggaga gtctgctgga cgtgttctcc ggttttata agtgtgatat   1080
tcattatgac tgtctacaat agttcgttca agccaattca aatggctagc tacactttcc   1140
cctggtggag tgttattttg ggttggttcc tgagacttct ctcagtcctc gcaattcctg   1200
```

-continued

```
tcttcgcaat aatctacctg ctcagcggta ccggcacact ttacgaacgc ttccgatggg    1260
caataactcc tcaacaacgc cgaaattcgg cgacttctct cgccgctgat cccacacaaa    1320
ttatcgatag ttctctttta gatccaattc atacacttac tccagtttag              1370
```

<210> SEQ ID NO 5
<211> LENGTH: 671
<212> TYPE: PRT
<213> ORGANISM: Caenorhabditis elegans

<400> SEQUENCE: 5

| | | | | | | | | | | | | | | |
|---|---|---|---|---|---|---|---|---|---|---|---|---|---|---|
| Met | Leu | Arg | Trp | His | Ser | Val | Arg | Arg | Lys | Gln | His | Gln | Gln | Leu | Gln |
| 1 | | | | 5 | | | | | 10 | | | | | 15 | |
| Ala | Glu | Leu | Ser | Ser | Gly | Ala | Ala | Ser | Met | Leu | Ser | Ala | Pro | Glu | Ser |
| | | | 20 | | | | | 25 | | | | | 30 | | |
| Arg | Arg | Val | Ser | Arg | Ser | Met | Ser | Val | Lys | Ala | Pro | Thr | Ala | Ser | Glu |
| | | | 35 | | | | | 40 | | | | | 45 | | |
| Tyr | Met | Pro | Leu | Ser | Val | Ala | Asp | Lys | Pro | Leu | Thr | Leu | Thr | Val | Ser |
| | 50 | | | | | 55 | | | | | 60 | | | | |
| Thr | Ser | His | Ser | Ile | Asp | Pro | Asn | Glu | Pro | Ile | Ala | Ala | Leu | Gly | Gly |
| 65 | | | | | 70 | | | | | 75 | | | | | 80 |
| Leu | Thr | Pro | Thr | Lys | Glu | Gly | Arg | Val | Ala | Ala | Leu | Arg | Arg | Arg | Ser |
| | | | | 85 | | | | | 90 | | | | | 95 | |
| Ser | Met | Val | Arg | Asp | Lys | Trp | Ala | Thr | Lys | Met | Glu | Phe | Leu | Leu | Ala |
| | | | 100 | | | | | 105 | | | | | 110 | | |
| Val | Val | Gly | Tyr | Ala | Val | Asp | Leu | Gly | Asn | Ile | Trp | Arg | Phe | Pro | Ser |
| | | | 115 | | | | | 120 | | | | | 125 | | |
| Val | Cys | Tyr | Lys | His | Gly | Gly | Gly | Ala | Phe | Leu | Ile | Pro | Tyr | Phe | Ile |
| | 130 | | | | | 135 | | | | | 140 | | | | |
| Met | Leu | Met | Ile | Gly | Gly | Leu | Pro | Met | Phe | Tyr | Met | Glu | Leu | Val | Leu |
| 145 | | | | | 150 | | | | | 155 | | | | | 160 |
| Gly | Gln | Phe | His | Arg | Ser | Gly | Cys | Val | Ser | Ile | Trp | Arg | Lys | Val | Cys |
| | | | | 165 | | | | | 170 | | | | | 175 | |
| Pro | Leu | Phe | Arg | Gly | Ile | Gly | Tyr | Gly | Ile | Cys | Cys | Ile | Cys | Thr | Phe |
| | | | 180 | | | | | 185 | | | | | 190 | | |
| Ile | Ala | Ile | Phe | Tyr | Asn | Ala | Ile | Ile | Ala | Gln | Ala | Val | Tyr | Phe | Ala |
| | | | 195 | | | | | 200 | | | | | 205 | | |
| Ile | Val | Ser | Leu | Ser | Lys | Ile | Trp | Asp | Ser | Glu | Val | Pro | Trp | Ala | Ser |
| | 210 | | | | | 215 | | | | | 220 | | | | |
| Cys | Gly | Asn | Pro | Trp | Asn | Thr | Pro | Arg | Cys | Ser | Asp | Asp | Leu | Asn | Val |
| 225 | | | | | 230 | | | | | 235 | | | | | 240 |
| Thr | Ile | Ser | Arg | Asn | Gly | Thr | Pro | Leu | Thr | Thr | Pro | Ser | Glu | Glu | Tyr |
| | | | | 245 | | | | | 250 | | | | | 255 | |
| Tyr | Leu | Tyr | Lys | Val | Leu | Glu | Val | Gln | Lys | Ser | Thr | Gly | Phe | Asp | Asp |
| | | | 260 | | | | | 265 | | | | | 270 | | |
| Leu | Gly | Gly | Val | Lys | Thr | Ser | Met | Ala | Val | Cys | Leu | Leu | Ala | Val | Phe |
| | | | 275 | | | | | 280 | | | | | 285 | | |
| Ile | Met | Val | Tyr | Phe | Ala | Leu | Trp | Lys | Gly | Pro | Gln | Ser | Ser | Gly | Lys |
| | 290 | | | | | 295 | | | | | 300 | | | | |
| Ile | Val | Trp | Val | Thr | Ala | Thr | Ala | Pro | Tyr | Ile | Ile | Leu | Ser | Ile | Leu |
| 305 | | | | | 310 | | | | | 315 | | | | | 320 |
| Leu | Ile | Arg | Gly | Leu | Leu | Pro | Gly | Ala | Lys | Asn | Gly | Leu | Tyr | Tyr |
| | | | | 325 | | | | | 330 | | | | | 335 | |
| Tyr | Val | Thr | Pro | Asp | Phe | Glu | Lys | Leu | Lys | Asp | Pro | Ala | Val | Trp | Ser |
| | | | 340 | | | | | 345 | | | | | 350 | | |

-continued

```
Ala Ala Ala Thr Gln Ile Phe Phe Ser Leu Gly Pro Gly Phe Gly Val
            355                 360                 365
Leu Leu Ala Leu Ser Ser Tyr Asn Asp Phe Asn Asn Asn Cys Tyr Arg
            370                 375                 380
Asp Ala Val Thr Ile Ser Ile Ile Asn Cys Ala Thr Ser Phe Phe Ser
385                 390                 395                 400
Gly Cys Val Val Phe Ser Thr Leu Gly Tyr Met Ser Leu Leu Thr Asn
                405                 410                 415
Lys Pro Ile Asn Glu Val Val Gly Glu His Asp Ala Ser Leu Ile Phe
            420                 425                 430
Ile Val Tyr Pro Gln Ala Leu Ala Thr Met Asp Tyr Ser Cys Phe Trp
            435                 440                 445
Ser Phe Ile Phe Val Met Leu Ile Thr Leu Gly Ile Asp Ser Thr
            450                 455                 460
Phe Ala Gly Ile Glu Ala Phe Ile Thr Gly Phe Cys Asp Glu Ser Arg
465                 470                 475                 480
Phe Leu Ser Lys Asn Arg Lys Trp Phe Val Leu Val Ile Cys Ile Ile
                485                 490                 495
Tyr Tyr Phe Leu Ser Phe Pro Ala Ile Ser Tyr Gly Gly Gln Phe Val
            500                 505                 510
Ile Pro Phe Leu Asp Glu Tyr Gly Val Ser Leu Ser Val Leu Phe Ile
            515                 520                 525
Val Thr Cys Glu Met Ile Ala Val Cys Trp Phe Tyr Gly Val Asp Gln
            530                 535                 540
Phe Ser Lys Asp Ile Arg Ala Met Leu Gly Phe Tyr Pro Gly Ile Tyr
545                 550                 555                 560
Trp Arg Val Cys Trp Thr Cys Ser Pro Val Phe Ile Ser Val Ile Phe
                565                 570                 575
Ile Met Thr Val Tyr Asn Ser Ser Phe Lys Pro Ile Gln Met Ala Ser
            580                 585                 590
Tyr Thr Phe Pro Trp Trp Ser Val Ile Leu Gly Trp Phe Leu Arg Leu
            595                 600                 605
Leu Ser Val Leu Ala Ile Pro Val Phe Ala Ile Ile Tyr Leu Leu Ser
            610                 615                 620
Gly Thr Gly Thr Leu Tyr Glu Arg Phe Arg Trp Ala Ile Thr Pro Gln
625                 630                 635                 640
Gln Arg Arg Asn Ser Ala Thr Ser Leu Ala Ala Asp Pro Thr Gln Ile
                645                 650                 655
Ile Asp Ser Ser Leu Leu Asp Pro Ile His Thr Leu Thr Pro Val
            660                 665                 670

<210> SEQ ID NO 6
<211> LENGTH: 224
<212> TYPE: PRT
<213> ORGANISM: Caenorhabditis elegans

<400> SEQUENCE: 6

Met Leu Arg Trp His Ser Val Arg Lys Gln His Gln Gln Leu Gln
1               5                   10                  15
Ala Glu Leu Ser Ser Gly Ala Ala Ser Met Leu Ser Ala Pro Glu Ser
            20                  25                  30
Arg Arg Val Ser Arg Ser Met Ser Val Lys Ala Pro Thr Ala Ser Glu
        35                  40                  45
Tyr Met Pro Leu Ser Val Ala Asp Lys Pro Leu Thr Leu Thr Val Ser
```

-continued

```
                    50                  55                  60
Thr Ser His Ser Ile Asp Pro Asn Glu Pro Ile Ala Ala Leu Gly Gly
 65                  70                  75                  80

Leu Thr Pro Thr Lys Glu Gly Arg Val Ala Ala Leu Arg Arg Arg Ser
                 85                  90                  95

Ser Met Val Arg Asp Lys Trp Ala Thr Lys Met Glu Phe Leu Leu Ala
            100                 105                 110

Val Val Gly Tyr Ala Val Asp Leu Gly Asn Ile Trp Arg Phe Pro Ser
            115                 120                 125

Val Cys Tyr Lys His Gly Gly Ala Phe Leu Ile Pro Tyr Phe Ile
            130                 135                 140

Met Leu Met Ile Gly Gly Leu Pro Met Phe Tyr Met Glu Leu Val Leu
145                 150                 155                 160

Gly Gln Phe His Arg Ser Gly Cys Val Ser Ile Trp Arg Lys Val Cys
                165                 170                 175

Pro Leu Phe Arg Gly Ile Gly Tyr Gly Ile Cys Cys Ile Cys Thr Phe
            180                 185                 190

Ile Ala Ile Phe Tyr Asn Ala Ile Ile Ala Gln Ala Val Tyr Phe Ala
            195                 200                 205

Ile Val Ser Leu Ser Lys Ile Trp Asp Ser Glu Val Pro Trp Ala Ser
210                 215                 220
```

<210> SEQ ID NO 7
<211> LENGTH: 671
<212> TYPE: PRT
<213> ORGANISM: Caenorhabditis elegans

<400> SEQUENCE: 7

```
Met Leu Arg Trp His Ser Val Arg Arg Lys Gln His Gln Gln Leu Gln
  1               5                  10                  15

Ala Glu Leu Ser Ser Gly Ala Ala Ser Met Leu Ser Ala Pro Glu Ser
             20                  25                  30

Arg Arg Val Ser Arg Ser Met Ser Val Lys Ala Pro Thr Ala Ser Glu
         35                  40                  45

Tyr Met Pro Leu Ser Val Ala Asp Lys Pro Leu Thr Leu Thr Val Ser
 50                  55                  60

Thr Ser His Ser Ile Asp Pro Asn Glu Pro Ile Ala Ala Leu Gly Gly
 65                  70                  75                  80

Leu Thr Pro Thr Lys Glu Gly Arg Val Ala Ala Leu Arg Arg Arg Ser
                 85                  90                  95

Ser Met Val Arg Asp Lys Trp Ala Thr Lys Met Glu Phe Leu Leu Ala
            100                 105                 110

Val Val Gly Tyr Ala Val Asp Leu Gly Asn Ile Trp Arg Phe Pro Ser
            115                 120                 125

Val Cys Tyr Lys His Gly Gly Ala Phe Leu Ile Pro Tyr Phe Ile
            130                 135                 140

Met Leu Met Ile Gly Gly Leu Pro Met Phe Tyr Met Glu Leu Val Leu
145                 150                 155                 160

Gly Gln Phe His Arg Ser Gly Cys Val Ser Ile Trp Arg Lys Val Cys
                165                 170                 175

Pro Leu Phe Arg Gly Ile Gly Tyr Gly Ile Cys Cys Ile Cys Thr Phe
            180                 185                 190

Ile Ala Ile Phe Tyr Asn Ala Ile Ile Ala Gln Ala Val Tyr Phe Ala
            195                 200                 205
```

-continued

```
Ile Val Ser Leu Ser Lys Ile Trp Asp Ser Glu Val Pro Trp Ala Ser
210                 215                 220
Cys Gly Asn Pro Trp Asn Thr Pro Arg Cys Ser Asp Asp Leu Asn Val
225                 230                 235                 240
Thr Ile Ser Arg Asn Gly Thr Pro Leu Thr Thr Pro Ser Glu Glu Tyr
            245                 250                 255
Tyr Leu Tyr Lys Val Leu Glu Val Gln Lys Ser Thr Gly Phe Asp Asp
            260                 265                 270
Leu Gly Gly Val Lys Thr Ser Met Ala Val Cys Leu Leu Ala Val Phe
            275                 280                 285
Ile Met Val Tyr Phe Ala Leu Trp Lys Gly Pro Gln Ser Ser Gly Lys
290                 295                 300
Ile Val Trp Val Thr Ala Thr Pro Tyr Ile Ile Leu Ser Ile Leu
305                 310                 315                 320
Leu Ile Arg Gly Leu Leu Pro Gly Ala Lys Asn Gly Leu Tyr Tyr
            325                 330                 335
Tyr Val Thr Pro Asp Phe Glu Lys Leu Lys Asp Pro Ala Val Trp Ser
            340                 345                 350
Ala Ala Ala Thr Gln Ile Phe Phe Ser Leu Gly Pro Gly Phe Gly Val
            355                 360                 365
Leu Leu Ala Leu Ser Ser Tyr Asn Asp Phe Asn Asn Asn Cys Tyr Arg
370                 375                 380
Asp Ala Val Thr Ile Ser Ile Asn Cys Ala Thr Ser Phe Phe Ser
385                 390                 395                 400
Gly Cys Val Val Phe Ser Thr Leu Gly Tyr Met Ser Leu Leu Thr Asn
            405                 410                 415
Lys Pro Ile Asn Glu Val Val Gly Glu His Asp Ala Ser Leu Ile Phe
            420                 425                 430
Ile Val Tyr Pro Gln Ala Leu Ala Thr Met Asp Tyr Ser Cys Phe Trp
            435                 440                 445
Ser Phe Ile Phe Phe Val Met Leu Ile Thr Leu Gly Ile Asp Ser Thr
450                 455                 460
Phe Ala Gly Ile Glu Ala Phe Ile Thr Gly Phe Cys Asp Glu Ser Arg
465                 470                 475                 480
Phe Leu Ser Lys Asn Arg Lys Trp Phe Val Leu Val Ile Cys Ile Ile
            485                 490                 495
Tyr Tyr Phe Leu Ser Phe Pro Ala Ile Ser Tyr Gly Gly Gln Phe Val
            500                 505                 510
Ile Pro Phe Leu Asp Glu Tyr Gly Val Ser Leu Ser Val Leu Phe Ile
            515                 520                 525
Val Thr Cys Glu Met Ile Ala Val Cys Trp Phe Tyr Gly Val Asp Gln
530                 535                 540
Phe Ser Lys Asp Ile Arg Ala Met Leu Gly Phe Tyr Pro Gly Ile Tyr
545                 550                 555                 560
Trp Arg Val Cys Trp Thr Cys Ser Ser Val Phe Ile Ser Val Ile Phe
            565                 570                 575
Ile Met Thr Val Tyr Asn Ser Ser Phe Lys Pro Ile Gln Met Ala Ser
            580                 585                 590
Tyr Thr Phe Pro Trp Trp Ser Val Ile Leu Gly Trp Phe Leu Arg Leu
            595                 600                 605
Leu Ser Val Leu Ala Ile Pro Val Phe Ala Ile Ile Tyr Leu Leu Ser
610                 615                 620
Gly Thr Gly Thr Leu Tyr Glu Arg Phe Arg Trp Ala Ile Thr Pro Gln
```

```
                625                 630                 635                 640
Gln Arg Arg Asn Ser Ala Thr Ser Leu Ala Ala Asp Pro Thr Gln Ile
                    645                 650                 655
Ile Asp Ser Ser Leu Leu Asp Pro Ile His Thr Leu Thr Pro Val
                660                 665                 670

<210> SEQ ID NO 8
<211> LENGTH: 60
<212> TYPE: PRT
<213> ORGANISM: Caenorhabditis elegans

<400> SEQUENCE: 8

Met Leu Arg Trp His Ser Val Arg Arg Lys Gln His Gln Gln Leu Gln
1               5                   10                  15
Ala Glu Leu Ser Ser Gly Ala Ala Ser Met Leu Ser Ala Pro Glu Ser
                20                  25                  30
Arg Arg Val Ser Arg Ser Met Ser Val Lys Asp Thr Lys Ser Leu Lys
                35                  40                  45
Phe Lys Asn Gln Gln Asp Ser Met Ile Leu Glu Val
        50                  55                  60

<210> SEQ ID NO 9
<211> LENGTH: 421
<212> TYPE: PRT
<213> ORGANISM: Caenorhabditis elegans

<400> SEQUENCE: 9

Met Leu Arg Trp His Ser Val Arg Arg Lys Gln His Gln Gln Leu Gln
1               5                   10                  15
Ala Glu Leu Ser Ser Gly Ala Ala Ser Met Leu Ser Ala Pro Glu Ser
                20                  25                  30
Arg Arg Val Ser Arg Ser Met Ser Val Lys Ala Pro Thr Ala Ser Glu
                35                  40                  45
Tyr Met Pro Leu Ser Val Ala Asp Lys Pro Leu Thr Leu Thr Val Ser
        50                  55                  60
Thr Ser His Ser Ile Asp Pro Asn Glu Pro Ile Ala Ala Leu Gly Gly
65                  70                  75                  80
Leu Thr Pro Thr Lys Glu Gly Arg Val Ala Ala Leu Arg Arg Arg Ser
                85                  90                  95
Ser Met Val Arg Asp Lys Trp Ala Thr Lys Met Glu Phe Leu Leu Ala
                100                 105                 110
Val Val Gly Tyr Ala Val Asp Leu Gly Asn Ile Trp Arg Phe Pro Ser
                115                 120                 125
Val Cys Tyr Lys His Gly Gly Ala Phe Leu Ile Pro Tyr Phe Ile
            130                 135                 140
Met Leu Met Ile Gly Gly Leu Pro Met Phe Tyr Met Glu Leu Val Leu
145                 150                 155                 160
Gly Gln Phe His Arg Ser Gly Cys Val Ser Ile Trp Arg Lys Val Cys
                165                 170                 175
Pro Leu Phe Arg Gly Ile Gly Tyr Gly Ile Cys Cys Ile Cys Thr Phe
                180                 185                 190
Ile Ala Ile Phe Tyr Asn Ala Ile Ile Ala Gln Ala Val Tyr Phe Ala
                195                 200                 205
Ile Val Ser Leu Ser Lys Ile Trp Asp Ser Glu Val Pro Trp Ala Ser
                210                 215                 220
Cys Gly Asn Pro Trp Asn Thr Pro Arg Cys Ser Asp Asp Leu Asn Val
```

-continued

```
                225                 230                 235                 240
Thr Ile Ser Arg Asn Gly Thr Pro Leu Thr Thr Pro Ser Glu Glu Tyr
                245                 250                 255

Tyr Leu Tyr Lys Val Leu Glu Val Gln Lys Ser Thr Gly Phe Asp Asp
                260                 265                 270

Leu Gly Gly Val Lys Thr Ser Met Ala Val Cys Leu Leu Ala Val Phe
                275                 280                 285

Ile Met Val Tyr Phe Ala Leu Trp Lys Gly Pro Gln Ser Ser Gly Lys
                290                 295                 300

Ile Val Trp Val Thr Ala Thr Ala Pro Tyr Ile Ile Leu Ser Ile Leu
305                 310                 315                 320

Leu Ile Arg Gly Leu Leu Leu Pro Gly Ala Lys Asn Gly Leu Tyr Tyr
                325                 330                 335

Tyr Val Thr Pro Asp Phe Glu Lys Leu Lys Asp Pro Ala Val Trp Ser
                340                 345                 350

Ala Ala Ala Thr Gln Ile Phe Phe Ser Leu Gly Pro Gly Phe Gly Val
                355                 360                 365

Leu Leu Ala Leu Ser Ser Tyr Asn Asp Phe Asn Asn Asn Cys Tyr Arg
                370                 375                 380

Asp Ala Val Thr Ile Ser Ile Ile Asn Cys Ala Thr Ser Phe Phe Ser
385                 390                 395                 400

Gly Cys Val Val Phe Ser Thr Leu Gly Tyr Met Ser Leu Leu Thr Asn
                405                 410                 415

Lys Pro Ile Asn Glu
                420

<210> SEQ ID NO 10
<211> LENGTH: 630
<212> TYPE: PRT
<213> ORGANISM: Homo sapiens

<400> SEQUENCE: 10

Met Glu Thr Thr Pro Leu Asn Ser Gln Lys Gln Leu Ser Ala Cys Glu
1               5                   10                  15

Asp Gly Glu Asp Cys Gln Glu Asn Gly Val Leu Gln Lys Val Val Pro
                20                  25                  30

Thr Pro Gly Asp Lys Val Glu Ser Gly Gln Ile Ser Asn Gly Tyr Ser
                35                  40                  45

Ala Val Pro Ser Pro Gly Ala Gly Asp Asp Thr Arg His Ser Ile Pro
                50                  55                  60

Ala Thr Thr Thr Thr Leu Val Ala Glu Leu His Gln Gly Glu Arg Glu
65                  70                  75                  80

Thr Trp Gly Lys Lys Val Asp Phe Leu Leu Ser Val Ile Gly Tyr Ala
                85                  90                  95

Val Asp Leu Gly Asn Val Trp Arg Phe Pro Tyr Ile Cys Tyr Gln Asn
                100                 105                 110

Gly Gly Gly Ala Phe Leu Leu Pro Tyr Thr Ile Met Ala Ile Phe Gly
                115                 120                 125

Gly Ile Pro Leu Phe Tyr Met Glu Leu Ala Leu Gly Gln Tyr His Arg
                130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Ile Ala Ser Tyr Tyr
                165                 170                 175
```

-continued

```
Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
        210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
            275                 280                 285

Tyr Ile Ile Leu Ser Val Leu Leu Val Arg Gly Ala Thr Leu Pro Gly
        290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Gln Ile Phe Phe Ser
                325                 330                 335

Leu Gly Pro Gly Phe Gly Val Leu Leu Ala Phe Ala Ser Tyr Asn Lys
                340                 345                 350

Phe Asn Asn Asn Cys Tyr Gln Asp Ala Leu Val Thr Ser Val Val Asn
                355                 360                 365

Cys Met Thr Ser Phe Val Ser Gly Phe Val Ile Phe Thr Val Leu Gly
            370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
                420                 425                 430

Thr Leu Gly Leu Asp Ser Thr Phe Ala Gly Leu Glu Gly Val Ile Thr
            435                 440                 445

Ala Val Leu Asp Glu Phe Pro His Val Trp Ala Lys Arg Arg Glu Arg
450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
                500                 505                 510

Ser Trp Phe Tyr Gly Ile Thr Gln Phe Cys Arg Asp Val Lys Glu Met
            515                 520                 525

Leu Gly Phe Ser Pro Gly Trp Phe Trp Arg Ile Cys Trp Val Ala Ile
            530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
```

```
                    595                 600                 605
Ile Lys Ser Ile Thr Pro Glu Thr Pro Thr Glu Ile Pro Cys Gly Asp
    610                 615                 620

Ile Arg Leu Asn Ala Val
625                 630

<210> SEQ ID NO 11
<211> LENGTH: 622
<212> TYPE: PRT
<213> ORGANISM: Drosophila melanogaster

<400> SEQUENCE: 11

Met Asp Arg Ser Gly Ser Ser Asp Phe Ala Gly Ala Ala Ala Thr Thr
  1               5                  10                  15

Gly Arg Ser Asn Pro Ala Pro Trp Ser Asp Asp Lys Glu Ser Pro Asn
                 20                  25                  30

Asn Glu Asp Asp Ser Asn Glu Asp Asp Gly Asp His Thr Thr Pro Ala
             35                  40                  45

Lys Val Thr Asp Pro Leu Ala Pro Lys Leu Ala Asn Asn Glu Arg Ile
 50                  55                  60

Leu Val Val Ser Val Thr Glu Arg Thr Arg Glu Thr Trp Gly Gln Lys
 65                  70                  75                  80

Ala Glu Phe Leu Leu Ala Val Ile Gly Phe Ala Val Asp Leu Gly Asn
                 85                  90                  95

Val Trp Arg Phe Pro Tyr Ile Cys Tyr Gln Asn Gly Gly Gly Ala Phe
                100                 105                 110

Leu Val Pro Tyr Cys Leu Phe Leu Ile Phe Gly Gly Leu Pro Leu Phe
            115                 120                 125

Tyr Met Glu Leu Ala Leu Gly Gln Phe His Arg Cys Gly Cys Leu Ser
    130                 135                 140

Ile Trp Lys Arg Ile Cys Pro Ala Leu Lys Gly Val Gly Tyr Ala Ile
145                 150                 155                 160

Cys Leu Ile Asp Ile Tyr Met Gly Met Tyr Tyr Asn Thr Ile Ile Gly
                165                 170                 175

Trp Ala Val Tyr Tyr Leu Phe Ala Ser Phe Thr Ser Lys Leu Pro Trp
            180                 185                 190

Thr Ser Cys Asp Asn Pro Trp Asn Thr Glu Asn Cys Met Gln Val Thr
    195                 200                 205

Ser Glu Asn Phe Thr Glu Leu Ala Thr Ser Pro Ala Lys Glu Phe Phe
210                 215                 220

Glu Arg Lys Val Leu Glu Ser Tyr Lys Gly Asn Gly Leu Asp Phe Met
225                 230                 235                 240

Gly Pro Val Lys Pro Thr Leu Ala Leu Cys Val Phe Gly Val Phe Val
                245                 250                 255

Leu Val Tyr Phe Ser Leu Trp Lys Gly Val Arg Ser Ala Gly Lys Val
            260                 265                 270

Val Trp Val Thr Ala Leu Ala Pro Tyr Val Val Leu Ile Ile Leu Leu
    275                 280                 285

Val Arg Gly Val Ser Leu Pro Gly Ala Asp Glu Gly Ile Lys Tyr Tyr
290                 295                 300

Leu Thr Pro Glu Trp His Lys Leu Lys Asn Ser Lys Val Trp Ile Asp
305                 310                 315                 320

Ala Ala Ser Gln Ile Phe Phe Ser Leu Gly Pro Gly Phe Gly Thr Leu
                325                 330                 335
```

-continued

```
Leu Ala Leu Ser Ser Tyr Asn Lys Phe Asn Asn Asn Cys Tyr Arg Asp
            340             345             350

Ala Leu Ile Thr Ser Ser Ile Asn Cys Leu Thr Ser Phe Leu Ala Gly
            355             360             365

Phe Val Ile Phe Ser Val Leu Gly Tyr Met Ala Tyr Val Gln Lys Thr
            370             375             380

Ser Ile Asp Lys Val Gly Leu Glu Gly Pro Gly Leu Val Phe Ile Val
385             390             395             400

Tyr Pro Glu Ala Ile Ala Thr Met Ser Gly Ser Val Phe Trp Ser Ile
                405             410             415

Ile Phe Phe Leu Met Leu Ile Thr Leu Gly Leu Asp Ser Thr Phe Gly
                420             425             430

Gly Leu Glu Ala Met Ile Thr Ala Leu Cys Asp Glu Tyr Pro Arg Val
            435             440             445

Ile Gly Arg Arg Arg Glu Leu Phe Val Leu Leu Leu Ala Phe Ile
    450             455             460

Phe Leu Cys Ala Leu Pro Thr Met Thr Tyr Gly Gly Val Val Leu Val
465             470             475             480

Asn Phe Leu Asn Val Tyr Gly Pro Gly Leu Ala Ile Leu Phe Val Val
            485             490             495

Phe Val Glu Ala Ala Gly Val Phe Trp Phe Tyr Gly Val Asp Arg Phe
            500             505             510

Ser Ser Asp Val Glu Gln Met Leu Gly Ser Lys Pro Gly Leu Phe Trp
            515             520             525

Arg Ile Cys Trp Thr Tyr Ile Ser Pro Val Phe Leu Leu Thr Ile Phe
            530             535             540

Ile Phe Ser Ile Met Gly Tyr Lys Glu Met Leu Gly Glu Glu Tyr Tyr
545             550             555             560

Tyr Pro Asp Trp Ser Tyr Gln Val Gly Trp Ala Val Thr Cys Ser Ser
                565             570             575

Val Leu Cys Ile Pro Met Tyr Ile Ile Tyr Lys Phe Phe Ala Ser
            580             585             590

Lys Gly Gly Cys Arg Gln Arg Leu Gln Glu Ser Phe Gln Pro Glu Asp
            595             600             605

Asn Cys Gly Ser Val Val Pro Gly Gln Gln Gly Thr Ser Val
610             615             620
```